United States Patent [19]

Storace

[11] Patent Number: 4,991,763
[45] Date of Patent: * Feb. 12, 1991

[54] SURGICAL STAPLER

[75] Inventor: Anthony Storace, Norwalk, Conn.

[73] Assignee: Technalytics Inc., Montvale, N.J.

[*] Notice: The portion of the term of this patent subsequent to Sep. 8, 2004 has been disclaimed.

[21] Appl. No.: 197,618

[22] Filed: May 23, 1988

[51] Int. Cl.$^5$ .......................................... A61B 17/068
[52] U.S. Cl. ...................................... 227/177; 227/19; 227/119; 227/132
[58] Field of Search ........... 227/19, 116, 119, DIG. 1, 227/120, 175, 176, 177, 132; 128/334 R; 606/219, 220

[56] References Cited

U.S. PATENT DOCUMENTS

| | | |
|---|---|---|
| 1,977,282 | 10/1934 | Kruse . |
| 2,086,922 | 7/1937 | Peterson .............................. 227/119 |
| 2,231,539 | 2/1941 | Larsen . |
| 3,180,128 | 4/1965 | Faulkner . |
| 4,043,504 | 8/1977 | Hueil et al. ........................... 227/19 |
| 4,185,762 | 1/1980 | Froehlich ............................. 227/138 |
| 4,396,139 | 8/1983 | Hall et al. ............................. 227/19 |
| 4,478,362 | 10/1984 | Foslien ................................. 227/19 |
| 4,527,725 | 7/1985 | Foslien ................................. 227/19 |
| 4,592,498 | 6/1986 | Braun et al. .......................... 227/19 |
| 4,596,350 | 6/1986 | Smith et al. ........................... 227/19 |
| 4,691,853 | 9/1987 | Storace ................................. 227/19 |
| 4,789,090 | 12/1988 | Blake, III .............................. 227/19 |
| 4,796,793 | 1/1989 | Smith et al. ........................... 227/19 |
| 4,807,628 | 2/1989 | Peter et al. ......................... 128/334 R |

FOREIGN PATENT DOCUMENTS

| | | |
|---|---|---|
| 0040157 | 11/1981 | European Pat. Off. . |
| 0203375 | 3/1986 | European Pat. Off. . |
| 0041022 | 12/1986 | European Pat. Off. . |

*Primary Examiner*—Paul A. Bell
*Assistant Examiner*—Rinaldi Rada
*Attorney, Agent, or Firm*—Curtis & Morris & Safford

[57] ABSTRACT

A surgical stapler device of the so-called pistol grip type includes a stack of staples loaded into a lower cartridge in an orientation similar to a conventional paper stapler. A former rotates and turns a leading staple 90° or normal to its prior orientation in the stack of staples as the former slides between a start position and a first intermediate forward position. The former is further displaced to a second intermediate forward position wherein the staple is moved in its perpendicular orientation within the device to the forming position which in turn moves a lower anvil. The former is further displaceable to a third intermediate forward position wherein the staple is formed around a staple forming surface of the lower anvil. The former moves to the final forward position wherein the former cams the lower anvil downwardly separating the formed staple from the staple forming surface of the lower anvil and an anti-bow button of the former contacts the cross-arm of the leading staple and pushes the cross-arm of the leading staple into abutting engagement with a downwardly depending lip of an upper anvil to set the staple. After the staple has been set, the lower anvil and former return together to the anvil home position. During this return, the staple transport surface of the lower anvil ends its lateral return phase below the leading staple in the cartridge. Further retraction of the former allows the lower anvil to rise, lifting the leading staple from the cartridge level to the forming level. This surgical stapler also includes allowing for a varying mechanical advantage to accommodate the staple advance at a resonable hand force level and provision for adjusting the amount of tissue which is drawn up or approximated within the perimeter of the formed staple.

17 Claims, 16 Drawing Sheets

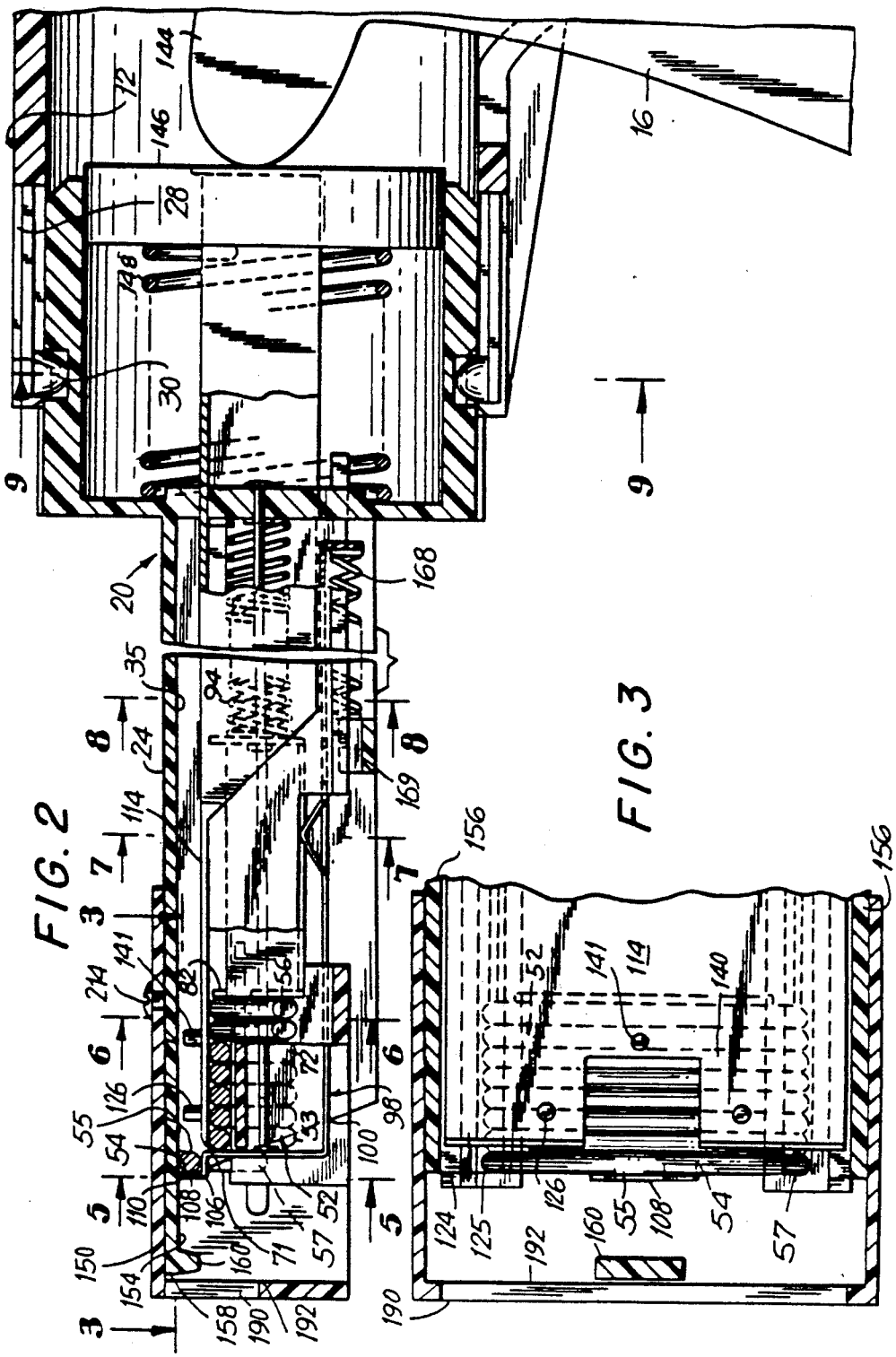

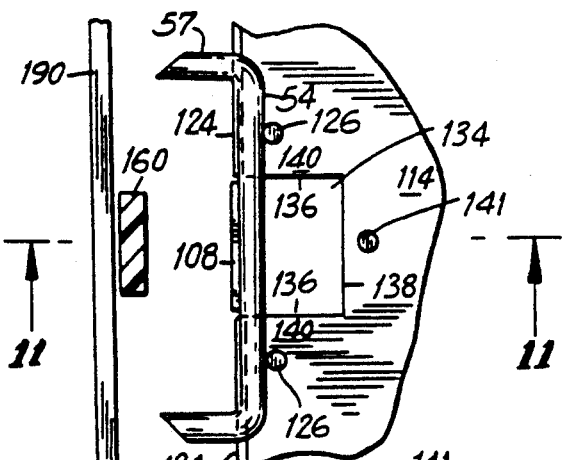
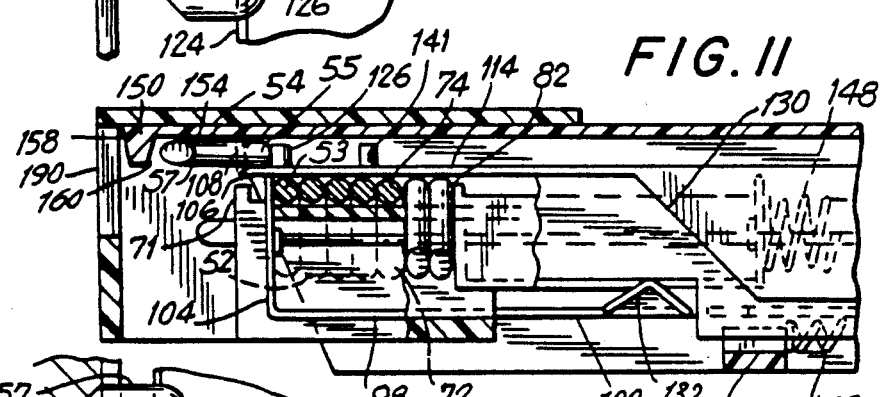
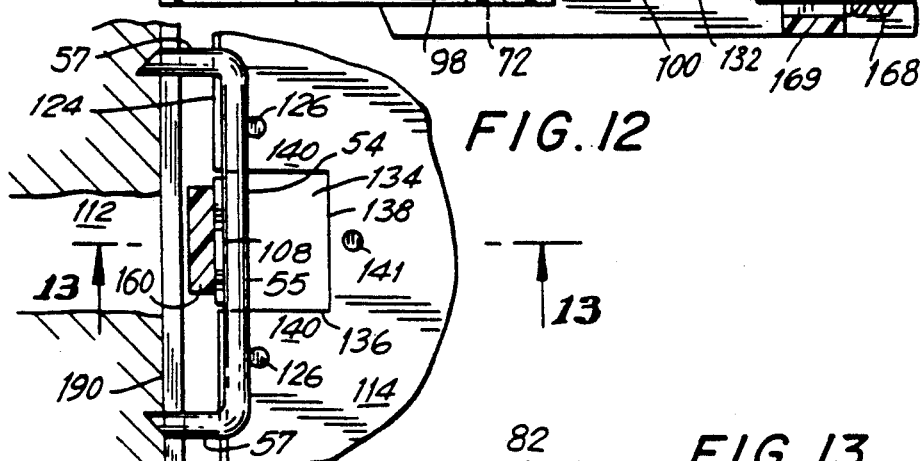
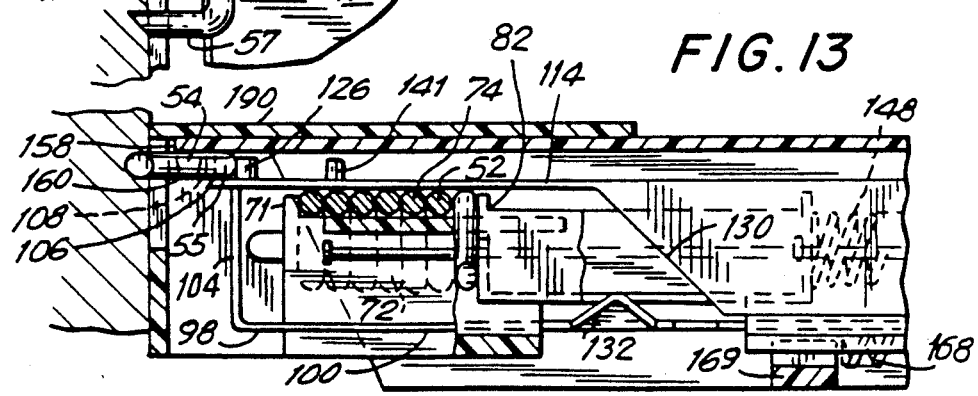

FORMER FORCE

FORMER SPRING FORCE

ANVIL SPRING FORCE

ANVIL TRAVEL

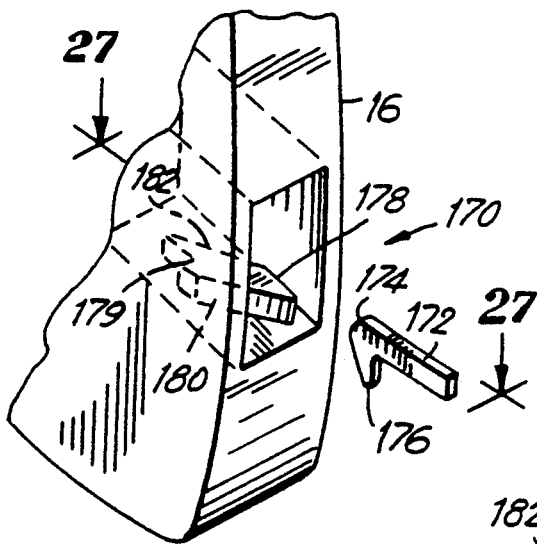
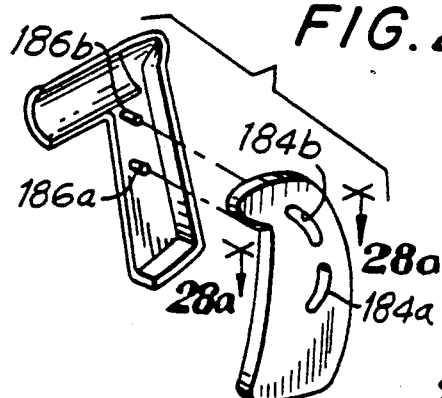
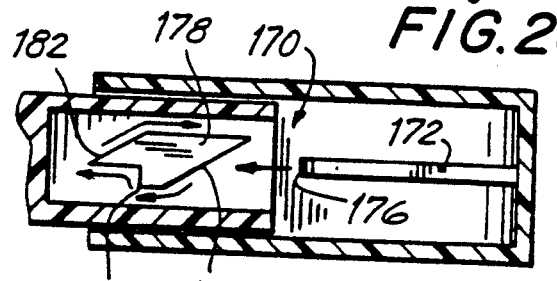
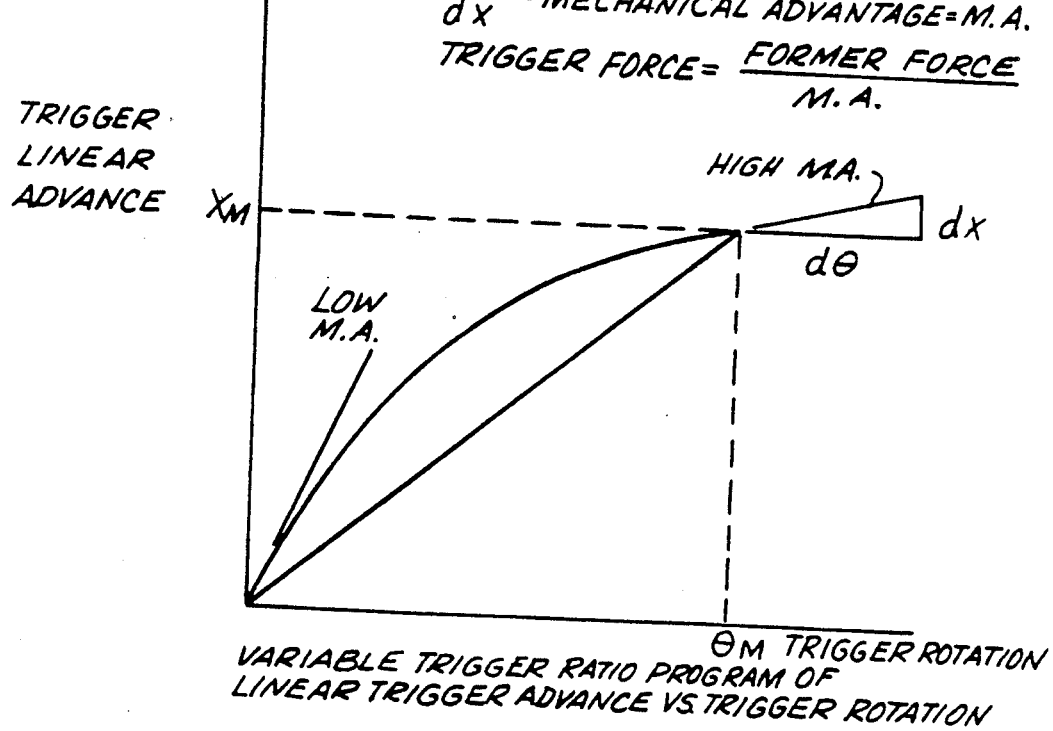

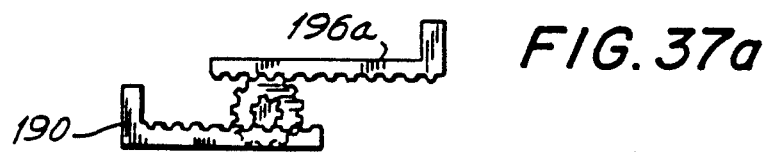
FIG. 37a
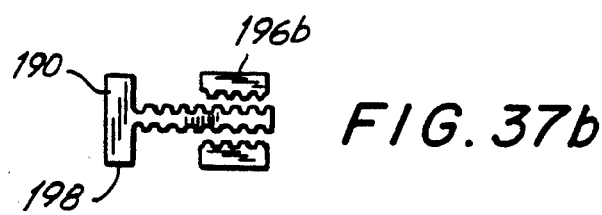
FIG. 37b
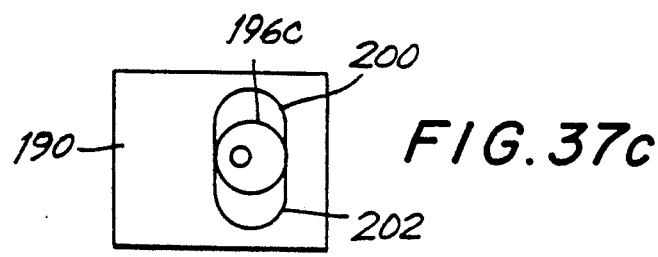
FIG. 37c
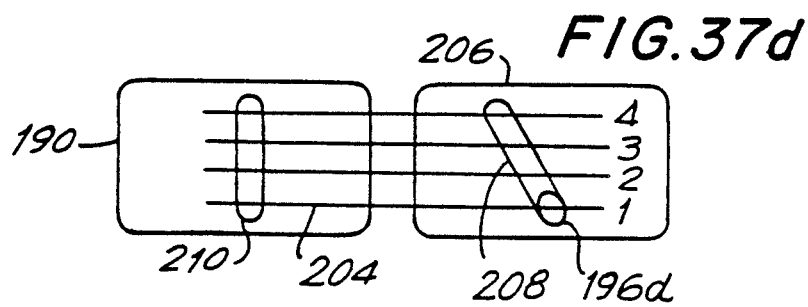
FIG. 37d
FIG. 38a
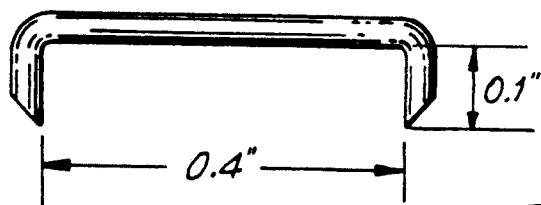
FIG. 38b
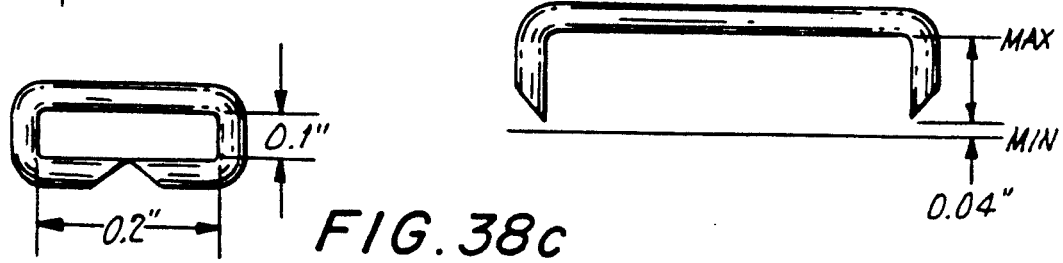
FIG. 38c

SURGICAL STAPLER

BACKGROUND OF THE INVENTION

This invention relates to a device for the closure of incisions at the conclusion of many typical surgical procedures. Such closures can involve the rejoining of a wide variety of tissue types and bones, such as the rib cage, fascia, muscle, skin and fat. Primary objectives of these closure procedures are to effect rapid and proper healing with a minimum of discomfort and scarring and to ensure that the wound remains securely closed. A related objective is that the closure not interfere with subsequent bandages and change of dressing.

Closure generally involves joining various layers of tissue, each in a special and correct manner. For instance, in abdominal surgery, the severed peritoneum layer must be joined, followed by the layers of muscle, fascia, fat and skin. Additionally, retention sutures which pass through all layers may be used or required as insurance that the closure will not open. To accomplish these sutured closures typical materials include silk, gut in a wide variety of synthetics including Dacron ®, Teflon ®, and various new disposable materials. Depending upon the strength required, the material may be monofilament or braided and the caliber may be varied. Also, there are metal sutures which are usually made from non-reactive stainless steel. Each material has characteristics which make its use appropriate for a specific purpose.

In all these techniques an important consideration is scar formation, the manner in which the human body reacts to suture materials which behave, for the most part, as foreign bodies and cause the body's defense mechanisms to seal them off with connective tissue. When the body's reaction is greater, more scar tissue will be formed.

Obviously, sutures cannot be passed without a delivery system which for these sutures consists of a large assortment of needles. Each type of needle is designed to provide a particular function, such as ease of handling, ease of passage, ease of release, minimal trauma, etc. The surgeon will generally either thread a needle or use pre-threaded suture-needle combinations in secondary instruments such as suture holders.

Wound closure is thus a major concern among surgeons and among the primary objectives of wound closure are: (a) to minimize time required to close, (b) to reduce surgeon fatigue and patient anesthesia time, (c) to reduce tissue trauma and accelerate wound healing, (d) to minimize blood loss, (e) to achieve optimum cosmetic results, and (f) to control and reduce overall costs.

These objectives have led to the development of a relatively new method of closure, namely, joining adjacent tissue with metal staples delivered and secured by a staple gun. These metal staples which have partially replaced traditional suture techniques, have become popular for both external and internal closures, including joining cut ends of blood vessels, hollow organs and various layers of tissue within the body. Dozens of stapling devices for surgery have been developed by Americans and others, especially workers in the Soviet Union.

One aspect of virtually all of these known stapling devices is the characteristic way in which they function and the use of bendable but nonresilient metal staples. Force is applied to change the initially open, generally U-shaped configuration of each metal staple to a final, closed configuration, so that the staple will hold two adjacent edges of tissue together. The staple devices are held and operated by the surgeon's hand, with force applied either manually by the surgeon or by a power-assisted manual force incorporated into the stapler. The force required to bend or crush the ends of the nonelastic metal staples is substantial, and is typically applied by a driver which drives each staple into position and then forcibly bends the legs of the staple. Once placed, the staples cannot be removed without the use of a separate device which forcibly returns the staple to its generally open configuration, so that removal is possible without tearing the tissue.

Applicant has previously invented a surgical stapler which utilizes a unique delivery system which provides a mode of increased control and includes provision for turning the staple generally normal to the plane of a stack of staples which are stacked as in a conventional paper stapler, to provide a more efficient and space-saving surgical stapler. The subject matter of such a stapler is disclosed in U.S. Pat. No. 4,691,853 issued Sept. 8, 1987. Practical experience with a working model of the invention described in U.S. Pat. No. 4,691,853 has led to several improvements described herein which will be perceived as advantages by the intended users, i.e. surgical personnel.

The improvements include advancing the staple within the case so that the rotation occurs within the housing, setting the staple at the end of the forward stroke, releasing the staple on the return stroke, provision for a varying mechanical advantage to accommodate the staple advance at a reasonable hand force level, and provision for adjusting the amount of tissue which is drawn up or approximated within the perimeter of the formed staple. This application, however, retains the original features in U.S. Pat. No. 4,691,853 of rotating the staple and stripping the lower anvil on the forward stroke using the surface of the former to restrain the staple.

OBJECTS OF THE INVENTION

It is a general object of this invention to provide a new and improved surgical stapler.

It is also an object of this invention to provide a surgical stapler which utilizes a unique delivery system which provides a mode of increased control and includes provision for turning the staple generally normal to the plane of the stack of staples to provide a more efficient and space-saving surgical stapler.

It is another object of this invention to provide a surgical stapler which achieves a reduction in overall size and weight of the stapler in order to provide a more exacting control for the surgeon, especially, in difficult-to-reach areas.

It is a further object of this invention to provide a surgical stapler which reduces the amount of manual force and motion applied to the device when it is at the site or delivery point of the staple so that it can be readily used by the surgeon without causing movement.

It is still a further object of this invention to provide a surgical stapler which advances the staple under a stabilizing compressive force after it has been rotated to position it at a significant distance from the staple magazine to allow the tip of the stapler to be angled to approximately 45° to the surface to be stapled.

It is still a further object of this invention to provide a surgical stapler which advances the staple after it has been rotated to a position at a sufficient distance from the staple magazine to allow the staple points to be contained within the case or housing while the staple is being rotated.

It is a still further object of this invention to provide a surgical stapler which releases the stapler on the return stroke of the former and as such permits the user to pull the wound edges taught for forceps tissue approximation after the staple is fully inserted but before the trigger is completely released.

It is a further object of this invention to provide a surgical stapler which strips the anvil from the staple on the forward stroke.

It is still a further object of this invention to provide a surgical stapler wherein the staple is set at the end of the forward stroke with the final stage of staple formation flattening the top of the staple cross-arm, and as a result thereof, reducing elastic springback of the staple and thus maintaining better control of the point gap.

It is another object of this invention to provide a surgical stapler having a preview latch which locks the stapling device against the action of the return springs and allows the user to comfortably position the staple points which in turn contributes to accurate staple placement.

It is a further object of this invention to provide a surgical stapler having a variable ratio trigger which transforms the variable or varying former force requirements into a more constant trigger force requirement and makes it possible to accommodate a relatively long trigger stroke.

It is yet a further object of this invention to provide a surgical stapler having a variable tissue shield which determines the volume of tissue which is finally drawn into the perimeter of the closed staple.

The present invention is directed towards solving these problems and provides a workable and economical solution to them. The new invention disclosed and claimed in subsequent sections of this application is fundamentally different from all known prior art stapling systems and devices.

SUMMARY OF THE INVENTION

The present invention is a hand-held and hand-operated multistage surgical instrument that carries a plurality of staples, preferably in a cartridge, and delivers and closes one staple at a time in the adjacent edges of an incision being closed or adjacent tissue or other substances being joined. This device is operated by squeezing a trigger a selected distance toward or into the case, and subsequently, releasing the trigger to automatically return to its normal position.

One end of a first or lower anvil is fixed to the cartridge retaining the stack of staples. The lower anvil includes a base having a cam follower surface projecting upwardly therefrom, a staple stack retainer surface extending upwardly from the end of the base in abutting relation with the stack of staples preventing horizontal movement of the stack of staples. The lower anvil also includes a staple transport surface extending generally outwardly from an end of the staple stack retaining surface, and a staple forming surface extending generally upwardly from the end of the staple transport surface.

A second or upper anvil is positioned generally above the first or lower anvil and below the upper surface of the case. The upper anvil includes a lip depending downwardly therefrom which aids in preventing ejection of the staple when the lower anvil is disengaged from the staple.

A staple former slideably advances within the case and includes a pair of arms extending outwardly therefrom which impinge upon the legs of the subject staple to turn the staple. In addition, a pair of projections extend upwardly therefrom and engage with the cross-arm of the staple to form the cross-arm during the forming process. Each arm includes a leg retaining edge to retain the staple during stripping from the lower anvil after forming. The former also includes a setting button extending upwardly therefrom which contacts the cross-arm of the staple and pushes the staple into abutting engagement with the downwardly depending lip of the upper anvil while at the same time eliminating undesired bowing of the cross-arm. The former further includes a cam extending downwardly therefrom which engages with the cam follower surface of the lower anvil for angular displacement of the lower anvil.

The former is displaceable between a start position wherein the legs of the staple are generally perpendicular to the plane of the former and generally parallel to the plane of the stack of staples and the cross-arm of the staple is reliably retained by the staple transport surface, and a first intermediate forward position wherein the legs of the former impinge upon the legs of the staple forcing the staple to rotate generally perpendicular to the plane of the stack of staples. The former is then moved to a second intermediate forward position wherein a pair of projections extending upwardly of the former move the turned staple until the lower anvil rests against the downwardly depending lip of the upper anvil or until the lower anvil forward motion is interrupted by the lower anvil abutting a forward stop. Subsequent thereto, the former is moved to a third intermediate forward position wherein the projections of the former engage the cross-arm of the staple and form the staple around the staple former surface of the lower anvil into a closed gripping configuration. In order to complete the forward stroke of the former, the former is moved to a final forward position wherein the former is advanced forwardly and the cam of the former engages the cam follower surface of the lower anvil cantilevering downwardly the free end of the lower anvil thereby disengaging the staple from the lower anvil, however, the staple is prevented from disengaging through the staple discharge area by the upper anvil. In addition, since the width of the upper anvil is slightly less than the width of the lower anvil, the staple does not bind onto the upper anvil allowing the staple to slide off the upper anvil when the former retracts. In this final forward position, a setting button extending upwardly from the former contacts the staple and pushes the staple onto the lip of the upper anvil. In this position, the final former advance flattens the bow of the cross-arm of the staple, which process is referred to as "setting the staple". This helps to maintain the staple points in close contact by reducing the elastic aftereffect known as "springback".

After the staple is set, the former cannot advance further. At the end of the forward stroke, the staple is constrained from ejection from the stapler by virtue of the lip of the upper anvil and the leg retention edges of the former. Since the staple is not disengaged at the end of the forward stroke, the surgeon is allowed to manipulate the wound edges prior to the release of the trigger. Upon release of the trigger, the lower anvil and the former return together to the lower anvil home position. During this return, in the flexed position, the staple transport surface of the anvil is displaced downwardly to thereby receive the next leading staple from the stack of staples. Further retraction of the former allows the lower anvil to be cantilevered upwardly thereby transporting the leading staple into a position for sequential stapling of the tissue.

In accordance with one of the general objects of this invention, it is desirable to latch the trigger just prior to staple formation. This preview latch locks the mechanism against the action of the return springs and allows the user to comfortably position the staple points, which are fully visible for insertion. The "preview latch" feature is based on two elements, namely, a flex arm molded as part of one side of the split case housing which includes a tip having a hooked section for hooking or latching the flex arm onto a latched recess in a raised cam feature molded into the trigger. At the trigger retained position, just prior to staple formation, the flexed flex arm springs laterally into the latch edge recess molded in the trigger cam. At this point, the trigger may be released and the flex arm hooked on the trigger cam will hold the case and trigger at a constant relative position against the action of the trigger return spring so that the user may comfortably position the staple points.

Since the force requirements of the former are different at varying stages of the forming process, the present invention includes a "variable ratio trigger". This "variable ratio trigger" not only drives the former in a straight line as the trigger rotates, but also provides for a low mechanical advantage early in the forward stroke and a high mechanical advantage during staple forming and setting at the end of the forward stroke. This variable ratio trigger design includes two pins which are molded into each half of the case and are located so as to engage two cam slots molded into the trigger. The trigger motion is determined by the shape of these cam slots. By proper design of the shape of the two cam tracks any desired program of rotation of trigger and linear trigger advance may be achieved.

The new stapler as disclosed herein also permits the surgeon to adjust and determine the volume of tissue which is finally drawn into the perimeter of the closed staple. This is known as "variable approximation". In one preferred embodiment, a tissue shield surrounding the staple discharge area is secured to the case and is slideably positioned relative to the staple points so as to adjust the distance between the front edge of the tissue shield and the staple points, which in turn, allows selection of the degree of tissue approximation. The tissue shield may be adjusted relative to the staple at the anvil position of staple formation by various means including, but not limited to, gears, screws and cams.

In another preferred embodiment to provide tissue approximation, the upper anvil location is varied, and as such, the case acts to shield the tissue varying the degree of tissue approximation. With this method, the upper anvil location is adjusted by the inclined cam technique wherein a slot on the case and a slot on the upper anvil are coupled via a slide button. As the button is slid from side to side, the upper anvil is cammed in and out thereby varying the amount of tissue approximation.

The new stapler as disclosed herein has many features which are significant and useful when used in the combination described above or in various other combinations. The new invention comprises first, a surgical stapler system wherein the stack of staples is configured in a typical orientation as those of a paper stapler and further includes a means of transporting, turning and forming the leading staple so that each staple may be discharged perpendicular to the stack of staples and such that the stapler may be used at great tilt-back angles.

The invention further comprises a delivery system, or apparatus to contain the staples, and to deliver, strip, and load them as required without having to use a crushing force. In addition, the improvements of this invention include advancing the staple so that the rotation occurs within the housing, setting the staple at the end of the forward stroke, and releasing the staple on the return stroke. Furthermore, this surgical stapler provides for varying mechanical advantages of the former to accommodate the staple advance at a reasonable hand force level and also provides a means for adjusting the amount of tissue which is drawn up or approximated within the perimeter of the formed staple.

Other objects and advantages of the invention will become apparent from the following detailed description and from the appended drawings in which like numbers have been used to describe like parts of the several views.

BRIEF DESCRIPTION OF THE DRAWINGS

The following detailed description, given by way of example but not intended to limit the invention solely to the specific embodiment described, may best be understood in conjunction with the accompanying drawings in which:

FIG. 2 is a cross-sectional view of the surgical stapler taken along line 2—2 of FIG. 1;

FIG. 3 is a partial top plan view of the surgical stapler taken along line 3—3 of FIG. 2;

FIG. 10 is a partial top plan view of the present invention showing the staple in the turned position;

FIG. 11 is a cross-sectional view of the present invention taken along line 11—11 of FIG. 10;

FIG. 12 is a partial plan view of the present invention similar to FIG. 10 showing the advance of the staple by the former from the cartridge location to the upper anvil location;

FIG. 13 is a cross-sectional view of the present invention taken along line 13—13 of FIG. 12;

FIG. 26 is a front perspective view of one preferred embodiment of the preview latch of this invention;

FIG. 27 is a top cross-sectional view taken along line 27—27 of FIG. 26;

FIG. 28 is a front perspective exploded view of the variable ratio trigger of this invention;

FIG. 28a is a cross-sectional view of the present invention taken along line 28a–28a of FIG. 28.

FIG. 29 is a chart depicting variable trigger ratio program of linear trigger advance versus trigger rotation;

FIGS. 37a, b, c and d are schematic representations of various kinematic mechanisms for varying the tissue shield of FIG. 33.

FIGS. 38 a–c are top elevational view illustrating the dimensions of a typical surgical staple.

DETAILED DESCRIPTION OF THE PREFERRED EMBODIMENT

Figure 1:
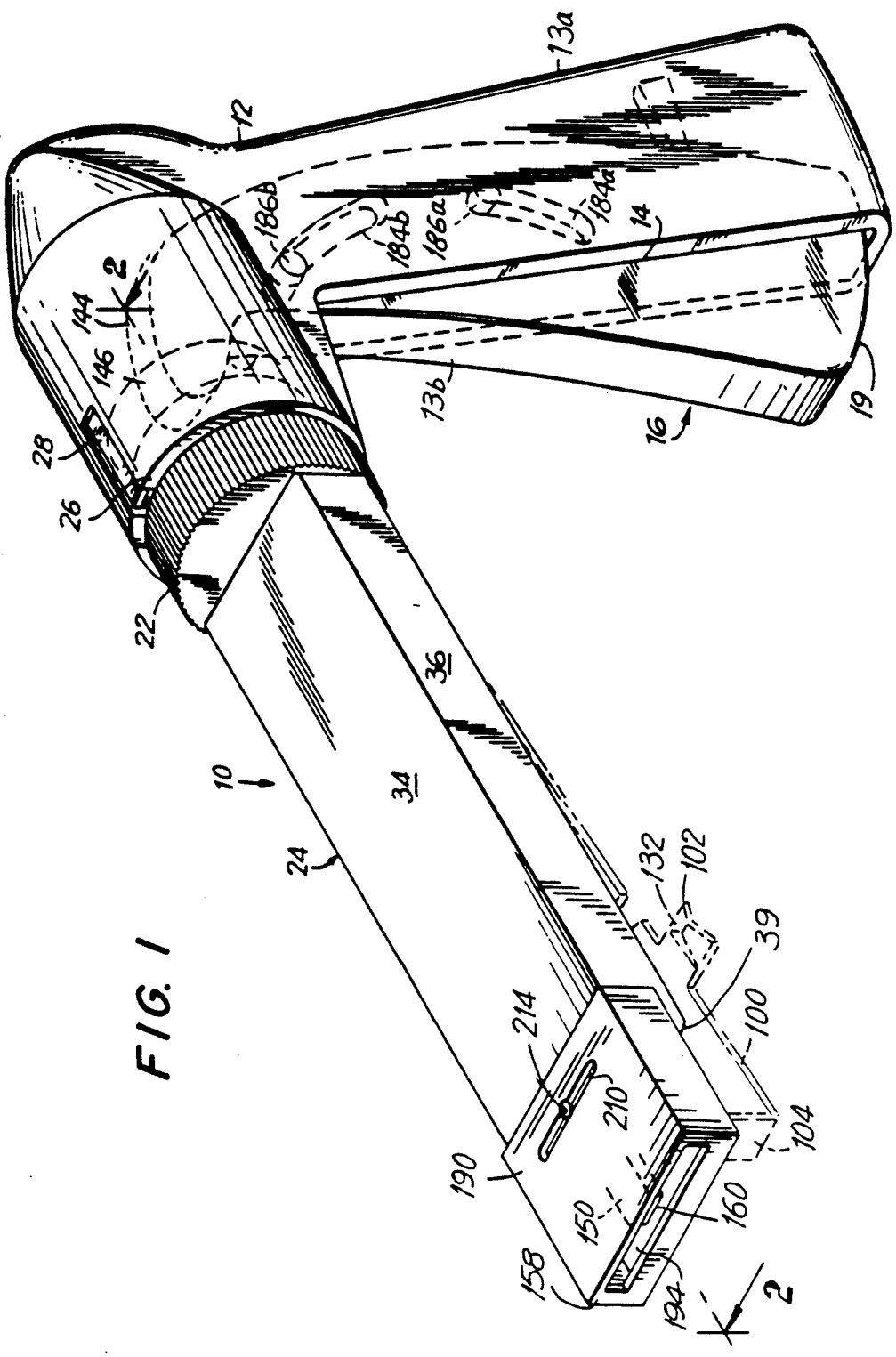
FIG. 1 is a front perspective view of one embodiment of the surgical stapler of this invention.

As shown in FIG. 1, a hand-held and hand-operated multistage surgical stapler 10 delivers and closes one staple at a time to the adjacent edges of an incision being closed or adjacent tissue or other substances being joined. Surgical stapler 10 is formed generally of a vertical case 12 having two halves 13a and 13b. The case has trigger opening 14 through which a trigger 16 is engageably inserted. Trigger 16 moves between a first extended position (shown in FIG. 1) and second retracted position upon hand pressure being applied on the trigger 16 by the surgeon. The bottom 19 of trigger 16 angles upwardly. FIG. 1 illustrates that trigger 16 is pivotable with about 30° of movement.

Figure 9:
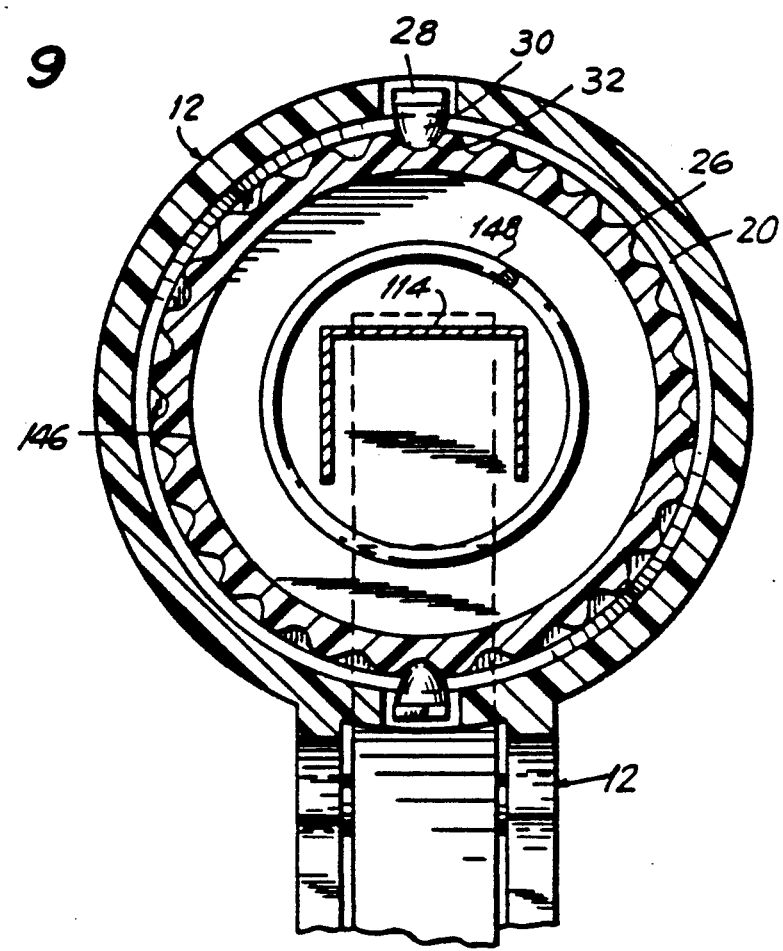
FIG. 9 is a front sectional view of the present invention taken along line 9—9 of FIG. 2.

The case of the stapler of the present invention also includes a barrel 20 having a cylindrical portion 22 and an upper cartridge housing 24. Cylindrical portion 22 includes a circumferential depression or cavity 26 formed therein, as best shown in FIGS. 3 and 9. Case 12 includes a plurality of tabs 28 extending outwardly therefrom and each tab 28 is provided with a head 30 depending downwardly therefrom. Cavity 26 is rotatably engaged by heads 30 of tabs 28 permitting rotational detent of the barrel 20 in relation to the case 12. Cavity 26 also includes a plurality of undulations 32, as best shown in FIG. 9, which provide a controllable orientation of the angular position of barrel 20. The surgeon may specifically direct a staple to the desired tissue as the barrel 20 "locks" at an angular orientation with minimum effort when head 30 is retained within undulation 32. With this invention, the surgeon has a free hand and need not restrain the barrel from further rotation with his free hand.

Upper cartridge housing 24 of case 12 includes a top face 34 and a bottom face or roof 35 and a pair of side faces 36 depending downwardly from the ends of top face 34. Upper cartridge housing 24 terminates in a front face 38 disposed adjacent to the staple discharge area. The front face 38 also includes an inclined portion 39 preferably with a 30° angle between the front face 38 and the bottom of the trigger 16.

Figure 4:
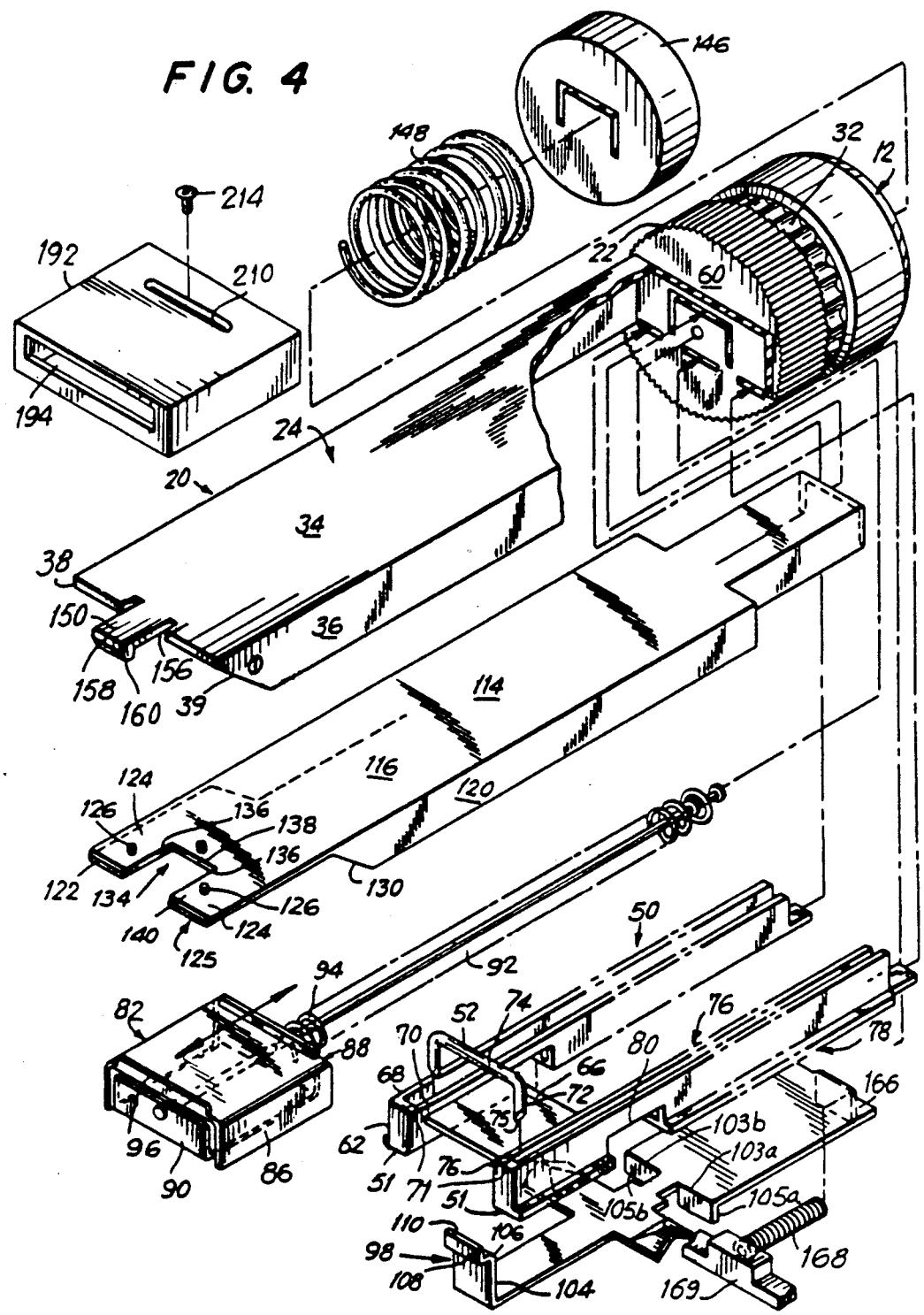
FIG. 4 is an exploded view of the case elements of one embodiment of the surgical stapler of the present invention.

As shown in FIGS. 2 and 3, the forward portion of upper housing 24 of the case covers a lower cartridge 50, a stack of staples 52, a pusher 82, a first or lower anvil 98, a former 114 and a second anvil 150. Lower cartridge 50 of the present invention, as best shown in FIG. 4, permits the stack of staples 52 to be retained and stacked as in a conventional paper stapler which allows for reasonably manufacturing dimensions and saves critical space in a surgical stapler. The stack of staples 52 includes a first staple 53 and a last or final staple 56. The rear wall 58 of the lower cartridge 50 is connected to the base plate 60 of the case 12.

Figure 5:
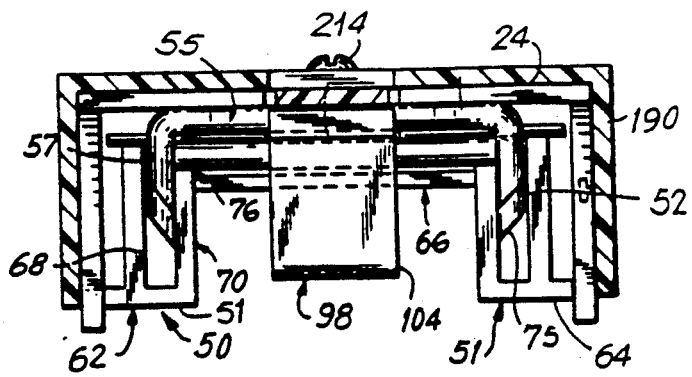
FIG. 5 is a front sectional view of the present invention taken along line 5—5 of FIG. 2.

Lower cartridge 50 includes a first symmetrical U-shaped channel 62 and a second symmetrical U-shaped channel 64. The first and second U-shaped channels 62 and 64 are connected by a middle web member 66 which provides support for channels 62 and 64. Channels 62 and 64 include outer facing legs 68 and inner facing legs 70 with outer facing legs 68 being greater in height than the inner facing legs 70. The legs 72 of stack of staples 52 are inserted between the outer and inner facing legs 68 and 70, respectively, and the cross-arm 74 of staples 52 abut and are retained by the top edge 76 of inner facing legs 70. As best shown in FIG. 5, the points 75 of the staples 52 do not contact the floor 51 of lower cartridge 50. This prevents frictional drag of the staples 52 in relation to lower cartridge 50 and permits lower cartridge 50 to be made of plastic or a plastic-like material. The lower cartridge 50 also includes a pair of side flanges 78 extending outwardly from the outer facing legs 70 for abutting engagement with side faces 36 of upper cartridge 24. The side flanges 78 extend along the entire length of channels 68 and 70 with the exception of a centrally located groove 80.

The present invention also includes a pusher 82 having a top face 84, side faces 86, rear face 88, and front face 90. A rod 92 is centrally positioned through the pusher assembly 82 and has one end connected to rear face 88 and its free end connected to base plate 60 of case 12. Pusher 82 is displaceable between rearward and forward positions by a pusher spring 94 disposed about rod 92 which is in biasing relationship with rear face 88. Front face 90 of pusher 82 includes an upwardly extending section 96 which abuts and is adjacent to the last or final staple 56 of the stack of staples 52 being retained within lower cartridge 50.

Figure 6:
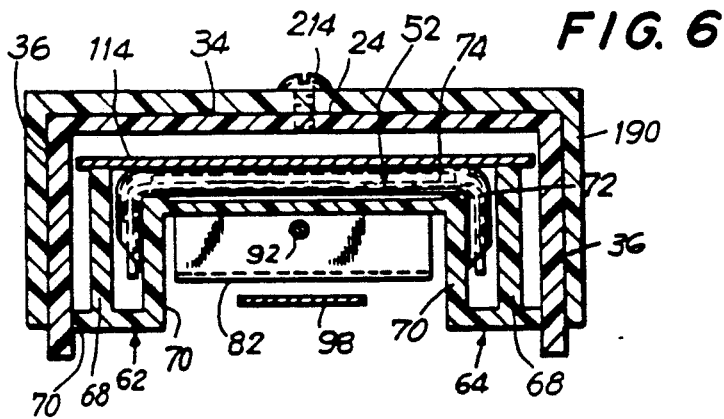
FIG. 6 is a front sectional view of the present invention taken along line 6—6 of FIG. 2.
Figure 7:
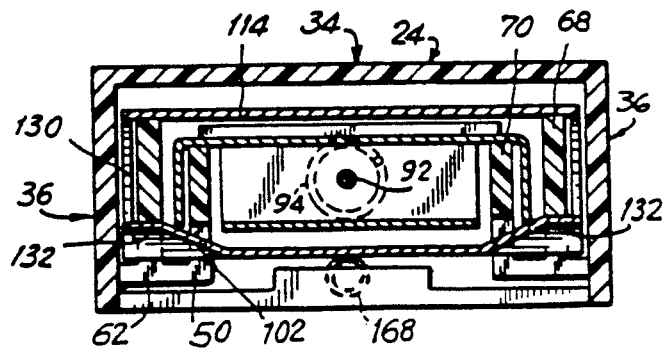
FIG. 7 is a front sectional view of the present invention taken along line 7—7 of FIG. 2.

Within the surgical stapler assembly 10, a first or lower anvil 98 is positioned generally below lower cartridge 50, as shown in FIG. 6, and between first and second U-shaped channels 68 and 70. Lower anvil 98 includes a base 100 having a pair of side arms 102 extending outwardly therefrom. Side arms 102 are received by and positioned within groove 80 of lower cartridge 50. Each rear face 103a and b of side arm 102 includes a flange 105a and b extending downwardly therefrom. A staple stack retainer surface 104 extends upwardly from an end of base 100 and retains stack of staples 52 from further movement as a result of the force being applied to the staples 52 by means of pusher 82. In the start position of the lower anvil, the staple stack retainer surface 104 generally abuts the first staple 53 within the stack 52. A staple transport surface 106 extends outwardly from staple stack retainer surface 104 and provides a surface for transporting the first staple 53 from stack 52 to a position where it can be turned, transported, and formed. A staple forming surface 108 extends upwardly from the staple transport surface 106 terminating at a free end 110. The staple forming surface 108 provides a surface wherein the subject or leading staple 54 may be formed around the lower anvil 98 into a generally rectangular configuration for insertion within the incision or wound 112 (See FIGS. 14 and 15).

A second or upper anvil 150 is secured to case 12 and is positioned below the upper cartridge housing 24 and generally above the first or lower anvil 98. The upper anvil includes a top surface 150 which directly abuts the bottom face 35 of upper cartridge housing 24, a bottom surface 154, side surfaces 156 and a front face 158 from which a lip 160 depends downwardly therefrom. The lip 160 aids the formed staple from being ejected after staple formation.

The surgical stapler 10 also includes a former 114 positioned within barrel 20 of case 12 between upper cartridge 24 and lower cartridge 50. Former 114 includes a top face 116, a bottom face 118, a pair of side faces 120 depending downwardly from the lateral edges of top face 116, and terminating in a front face 122. Outer facing legs 68 of lower cartridge 50 engage the bottom face 118 of former 114 retaining former 114 within barrel 20. Top face 116 of former 114 has a pair of arms 124 extending outwardly therefrom. Arms 124 impinge upon the leading staple 54 which is retained by the staple transport surface 106 and a pair of projections 126 extending above the plane of former 114, as shown in FIGS. 10 and 11. Arms 124 provide a means to turn leading staple 54 at least 90°, or normal to the position of the staple in the stack of staples 52 in lower cartridge 50, preferably, to ensure maximum clarity in the surgeon's line of vision when placing a staple in position.

Front face 125 of former 114 is chamfered to aid in rotating the leading staple 54. It is, of course, recognized that an angle less than 90° may still be utilized although an angle less than 90° will not be as beneficial in terms of providing a clear unimpeded sight line to staple placement. As a result of the ability to rotate the staples, the present invention utilizes a stack of staples which are in a conventional paper stapler orientation to reduce the space of the stapler and provide for reasonable manufacturing dimensions.

As best shown in FIGS. 12 and 13, in the preferred embodiment of this invention, the pair of projections 126 of former 114 extend into the plane of leading staple 54 and apply a force to the cross-arm 55 of staple 54 to move the leading staple as well as the lower anvil 98 until the first anvil 98 contacts the downwardly depending lip 160 of upper anvil 150 or until the lower anvil contacts its abutting forward stop. In this position, just prior to forming, the leading staple is retained by staple transport surface 106 and staple forming surface 108 of lower anvil 98, as well as the projections 126. Former 114 is subsequently advanced further such that projections 126 force the staple to be formed in a closed gripping configuration about the staple forming surface 108 of first anvil 98 within the incision or wound (See FIGS. 14 and 15).

Figure 16:
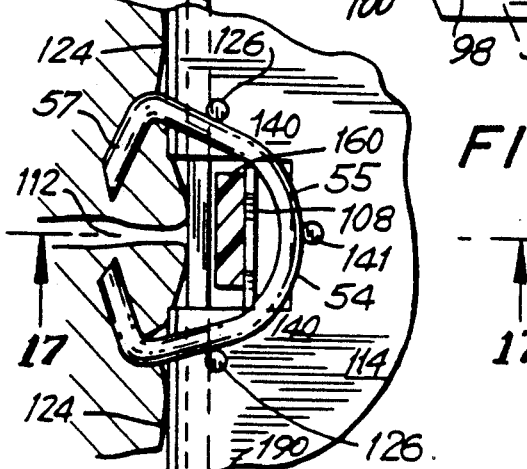
FIG. 16 is a partial top plan view of the present invention similar to FIG. 10 showing further advance of the former cams the lower anvil downwardly thereby disengaging the lower anvil from the staple.
Figure 17:
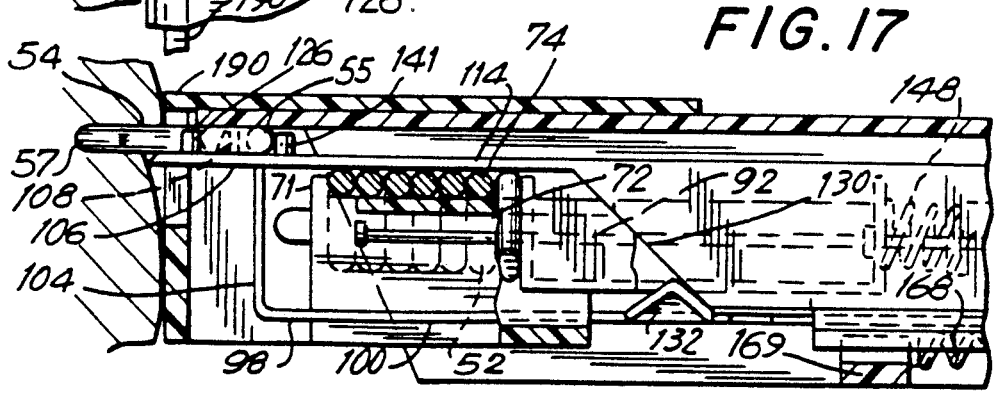
FIG. 17 is a cross-sectional view of the present invention taken along line 17—17 of FIG. 16.

The former further includes a cam 130 inclined upwardly along the side faces 120 of former 114. Cam 130 engages a cam follower surface 132 of lower anvil 98 which extends upwardly from the ends of side arms 102 of lower anvil 98 when former 114 advances to bend or cantilever downwardly the lower anvil. The relationship between cam 130 and cam follower 132 is best shown in FIGS. 16 and 17.

An opening 134 is formed between arms 124 of former 114. Opening 134 includes side edges 136 depending inwardly from front face 122 of former 114 and rear edge 138. The area of arms 124 between projections 126 and each side edge 136 define a leg retaining surface or edge 140.

As aforementioned, subsequent movement of the former causes the cam 130 to engage the cam follower surface 132 thereby cantilevering downwardly the lower anvil 98. A setting button 141 contacts the cross-arm 55 of leading staple 52 and moves the cross-arm into abutting engagement with downwardly depending lip 160 of upper anvil 150. This final former advance flattens the bow of the cross-arm of the staple, which process is referred to as "setting the staple". This helps to maintain the staple points in close contact by reducing the elastic aftereffect known as "springback".

After the staple is set, the former cannot advance further. At the end of the forward stroke, the staple is retained within the stapler by virtue of the lip 160 of upper anvil 150 and the leg retaining surfaces 140 of former 114. As such, at the end of the forward stroke, the user is still able to manipulate the wound edges prior to the release of the trigger.

During return, the lower anvil 98 and former 114 return together to the lower anvil home position. The lower anvil remains in its stripped position flexed downwardly from the plane of former 114. During this return, the staple transport surface 106 of lower anvil 98 ends its lateral return phase below the next leading staple 53 in the lower cartridge 50. Further retraction of former 114 allows the lower anvil 98 to rise lifting the leading staple 52 from the lower cartridge level to the forming level. As such, a stapling operation has been completed.

Bottom face 118 of former 114 tightly abuts the top of the cross-arms of the stack of staples 52. Such an arrangement provides for space saving within the surgical stapler 10 and also allows leading staple 54 to be inserted within the wound or incision 142 at a greater angle to the tissue to be stapled as the farther the staple is moved upwardly into a position to be turned, the less tilt-back angle is permitted with the skin surface to ensure proper stapling.

A ball 144 of trigger 16 engages a load button 146 which causes former 114 to advance in a straight line motion. A first or main spring 148 which is in biasing relation with load button 146 causes trigger 116 and former 114 to return to their start position. As will be described herein, since the force requirements of the former are different at the varying sequence steps of the forming operation, a variable ratio trigger is also provided herein.

In use, the present invention is operated by squeezing a pivoting trigger 16 a selected distance towards or into case 12, and subsequently releasing trigger 16 to automatically return to its rest position. This motion of trigger 16 activates a multi-stage operation that includes the following steps: (a) turning the staple 54 to an orientation generally normal to the incision or wound for subsequent closure and ejection of the leading staple; (b) transporting the leading staple and the lower anvil a predetermined distance until restrained from further movement by the downwardly depending lip 160 of upper anvil 150; (c) forming the leading staple 54 around staple forming surface 108 of lower anvil 98 into a generally rectangular configuration closing legs of leading staple 54 within the incision or wound 112; (d) stripping the lower anvil 98 out of engagement with the cross-arm 55 of leading staple 54; (e) forcing the staple into contact with the downwardly depending lip 160 of upper anvil 150 and setting the staple by having setting button 141 of former 114 contact the bowed cross-arm of leading staple 54; (f) releasing the staple on a fully controlled basis into the tissue of the wound or incision 112 without having the staple retract with lower anvil 98; (g) returning the lower anvil and the former 114 to their home position such that the staple transport surface 108 of lower anvil 98 ends its lateral return phase below the leading staple in the staple cartridge 50; (h) loading first staple 53 from stack of staples 52 onto the staple transport surface 106 of lower anvil 98; (i) transporting leading staple 54 into a position where it can be turned generally normal to the plane of the stack of staples 52; and (j) turning a new staple as in paragraph (a) above to repeat stapling. Each of these steps will be described in detail below.

FIG. 2 illustrates the leading staple 54 in its starting position. The stack of staples 52 is retained within lower cartridge 50 with legs 72 of the staples depending generally downwardly. The cross-arms 74 of the stack of staples 52 are tightly retained by bottom face 118 of former 114. The pusher 82 upon the urging of pusher spring 94 exerts a force upon the stack of staples 52. The stack of staples 52 is restrained from further movement by staple stack retainer surface 104 of lower anvil 98.

Figure 8:
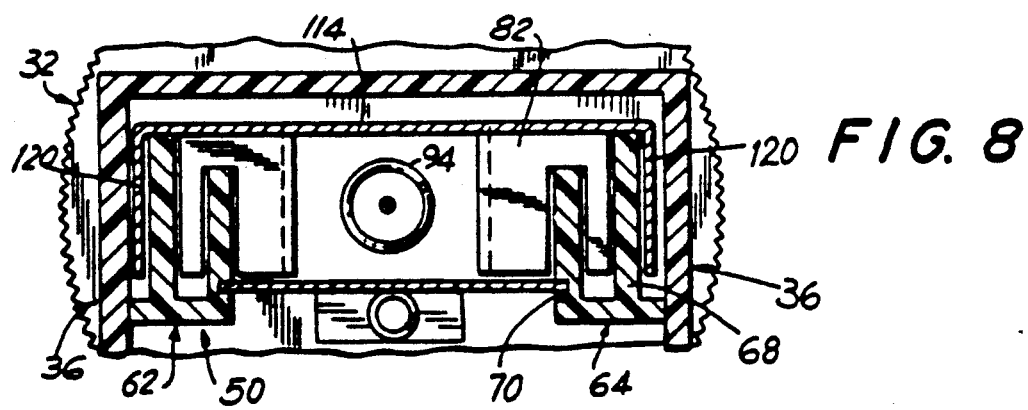
FIG. 8 is a front sectional view of the present invention taken along line 8—8 of FIG. 2.

As shown in FIG. 2, in its starting position, the leading staple 54 has its legs 57 depending generally downwardly generally parallel to legs 72 of the stack of staples 52. Leading staple 54 is retained within the opening defined by staple transport surface 106 of lower anvil 98 and the upwardly extending step 71 of lower cartridge 50. In the rest position, cam 130 of former 114 is recessed behind cam follower surface 132 of anvil 98 and does not engage cam follower surface 132 as illustrated in FIGS. 2 and 8.

As shown in FIGS. 2, 10 and 11, former 114 is displaceable between a start position, wherein the legs 57 of leading staple 54 are generally perpendicular to the plane of former 114 and parallel to the plane of the stack of staples 52 and cross-arm 55 of leading staple 54 is reliably retained between arms 124 of former 114, staple transport surface 106 of lower anvil 98, and bottom face 154 of upper anvil 150, and a first intermediate forward position, wherein legs or arms 124 of former 114 advance forwardly upon actuation of trigger 16 exerting a force upon load button 146. In the former first intermediate forward position, former arms or legs 124 impinge upon legs 57 of leading staple 54 so that legs 57 are turned upwardly in a plane generally normal to legs 72 in the stack of staples 52 and parallel to the plane of former 114.

After the loaded staple is turned or rotated, the former moves to a second intermediate forward position (FIGS. 12 and 13) wherein the projections 126 engage the cross-arm 55 of leading staple 54 which in turn pushes lower anvil 98 until lower anvil 98 contacts the downwardly depending lip 160 of upper anvil 150 or flanges 105a and b contact spring support or forward stop 169. After the lower anvil contacts the forward stop the lower anvil ceases to advance with the former 114 as will be described hereinafter.

Figure 14:
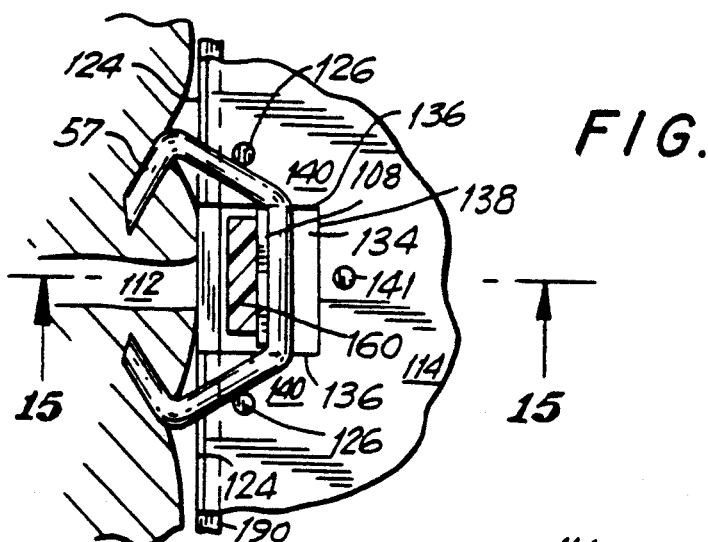
FIG. 14 is a partial top plan view of the present invention similar to FIG. 10 showing the staple being formed around the staple forming surface of the lower anvil.
Figure 15:
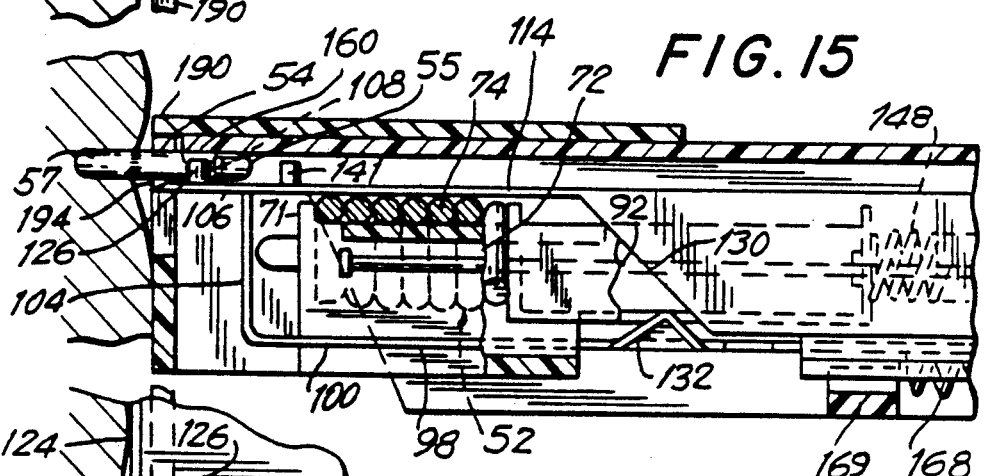
FIG. 15 is a cross-sectional view of the present invention taken along line 15—15 of FIG. 14.

FIGS. 14 and 15 illustrate the forming of leading staple 54 within the incision or wound 112. Former 114 advances further forwardly from the second intermediate forward position into a third intermediate forward position. In this third intermediate forward position projections 126 of former 114 advance forwardly and apply a force upon cross-arm 55 of leading staple 54. The staple 54 is formed around staple forming surface 108 of the lower anvil 98 into a generally rectangular configuration wherein legs 57 of staple 54 close adjacent one another within the incision or wound 112 (FIG. 15). The leading staple 54 is formed in a plane generally perpendicular to the plane of the stack of staples 52 and in a plane generally parallel to the plane of former 114. As illustrated in FIGS. 14 and 15, the staple in the formed position within the incision or wound 112 is retained within the surgical stapler 10 by staple forming surface 108, staple transport surface 106, and leg retaining surface or edge 140 on top face 116 of former 114. Of course, the leading staple 54 will also be retained by the tissue of the wound or incision 112.

During the process of forming the staple, the cross-arm of the staple has a tendency to bow up. This bowing must be allowed for in the dimensioning of the various former features which have been provided for in the present invention. As is shown in FIGS. 16 and 17, when the former is moved to a final forward position, the cam 130 of former 114 engages the cam follower surface 132 of anvil 114 cantilevering or bending downwardly lower anvil 98 disengaging the leading staple 54 from staple forming surface 108 of lower anvil 98 (See FIGS. 18 and 19). The staple, however, is prevented from disengaging with the stapler as a result of its placement with respect to the lip 160 of the upper anvil 150 as well as the leg retainer surfaces 140 of the former 114.

Figure 18:
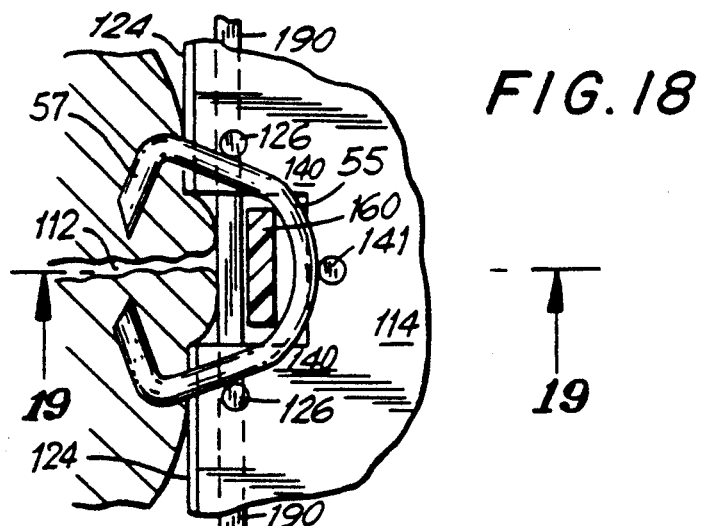
FIG. 18 is a partial top plan view of the present invention similar to FIG. 10 showing a setting button of the former pushing the formed staple in abutting engagement with the upper anvil.
Figure 19:
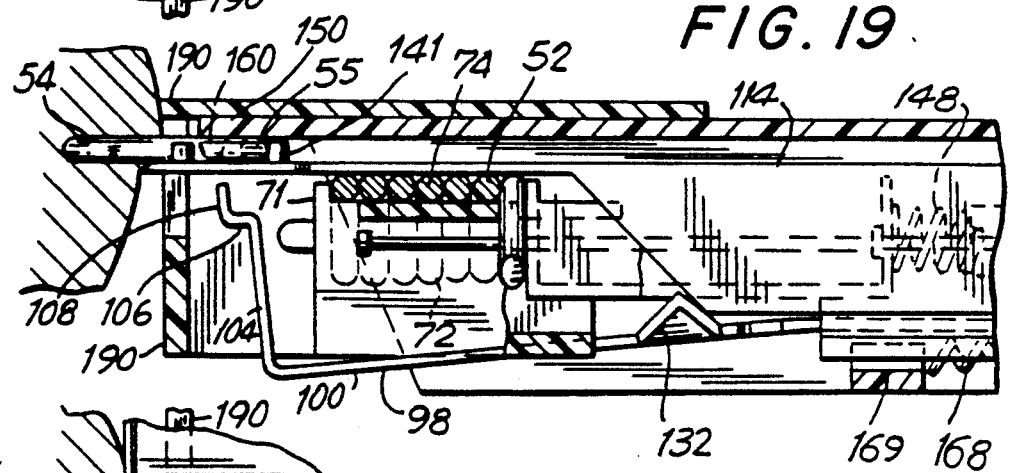
FIG. 19 is a cross-sectional view of the present invention taken along line 19—19 of FIG. 18.

Referring now to FIGS. 18 and 19, after the lower anvil has been cammed down sufficient to unblock the staple, in the final forward position a setting button 141 of former 114 contacts the staple at the former advance corresponding to the unblocking of the staple by the lower anvil. This setting button 141 pushes the staple into abutting engagement with the downwardly depending lip 160 of upper anvil 150. This final former advance flattens the bow of the cross-arm of 55 of leading staple 54, which process is referred to as "setting the staple". This helps to maintain the staple points in close contact by reducing the elastic aftereffect known as "springback".

Figure 24:
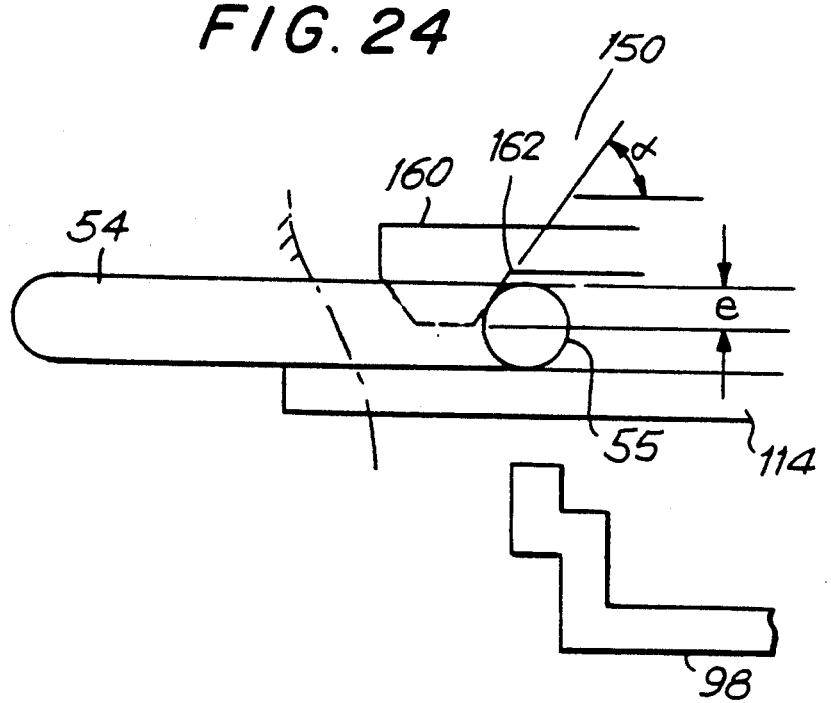
FIG. 24 is an enlarged side plan view of the former and upper anvil restraining the staple from moving after the lower anvil has been stripped.

As aforementioned, the staple is formed around the lower anvil and transfers onto the upper anvil after the lower anvil is cammed downwardly. The staple is finally set by the former against the upper anvil (see FIGS. 18–19). Since the upper anvil 150 is less wide than the lower anvil, frictional engagement between the staple and the upper anvil is prevented when the lower anvil is stripped from the staple. It also allows the upper anvil to easily disengage from the staple when the former retracts. To facilitate the disengagement of the upper anvil and the staple, the upper anvil is preferably shaped as shown in FIG. 24. The upper anvil has a chamfered edge 162 into which the cross-arm 55 of the leading staple abuts. By reducing the engagement of the upper anvil into the staple to a minimum consistent with good design practice and by angling the surfaces of the upper anvil, as shown in FIG. 24, the upper anvil may be made to easily disengage from the pinch between the staple on the one side and the approximated tissue on the other. It is important that the staple easily disengage from upper anvil 150 after the former retracts to avoid any so called "hang-up" in releasing the stapler from the tissue. In case of such "hang-up", the user is required to pull the stapler free, which action is obviously highly undesirable.

After the staple is set, the former cannot advance further. This is the end of the forward stroke. At the end of the forward stroke the staple is attached to the stapler by virtue of the downwardly depending lip 160 of upper anvil 150 and the leg retaining surfaces 140 of the former. This is in contrast to U.S. Pat. No. 4,691,853 where the staple is disengaged from the stapler at the end of the forward stroke. This system allows the user to manipulate the wound edges prior to release of the staple which will be discussed in more detail herein.

Figure 20:
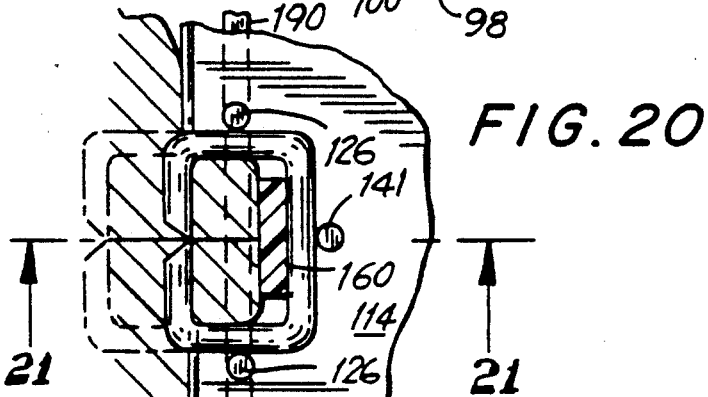
FIG. 20 is a partial top plan view of the present invention similar to FIG. 10 showing the partial return of the former wherein the lower anvil is capable of receiving the next leading staple from the stack of staples.
Figure 21:
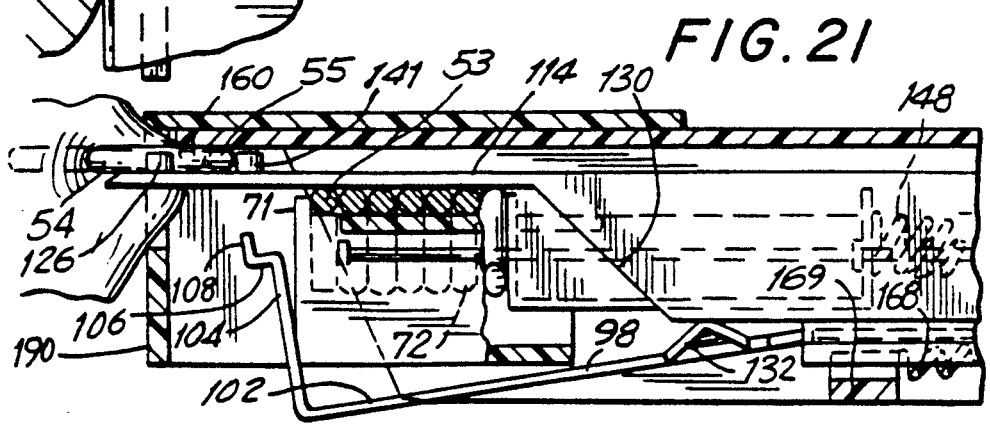
FIG. 21 is a cross-sectional view of the present invention taken along line 21—21 of FIG. 20.

As best shown in FIGS. 20 and 21, after the staple has been set, the lower anvil and the former partially return to their home position together. The lower anvil 98 returns to its home position as a result of the biasing force of anvil return spring 168 secured to spring support 169. During retraction, the lower anvil 98 remains in its stripped condition in a horizontal plane below the horizontal plane of former 114 to be capable of receiving the next leading staple 53 from stack of staples 52.

As the lower anvil and former complete the final phase of their return stroke, the staple transport surface 106 of lower anvil 98 moves downwardly so that it is at a vertical level generally in the plane of cross-arm 74 of first staple 53 within stack of staples 52. The first staple 53 within the stack of staples 52 is urged forwardly to be retained by staple transport surface 106 as a result of force applied by pusher 82 upon stack of staples 52. A built up ramp 71 on lower cartridge 50 aids in lifting the cross arm such that it can be easily received by the staple transport surface 106.

In order to complete one cycle, after the former retracts to a position rearward of the vertical plane of the staple transport surface 106, the lower anvil 98 is cantilevered or bent upwardly (see FIG. 2) transporting the leading staple 54 upwardly with its legs in a plane generally parallel to the plane of the stack of staples 52. The leading staple 54 is transported upwardly within the cavity defined by staple forming surface 108 and staple transport surface 106. The leading staple 54 is transported upwardly into the start position of the former as shown in FIG. 2 wherein the leading staple is retained within the opening defined by the upwardly extending step 71 of lower cartridge 50 and the staple transport surface 106. As such, the cycle is completed and further stapling repeats the above-mentioned cycle.

Figure 22A:
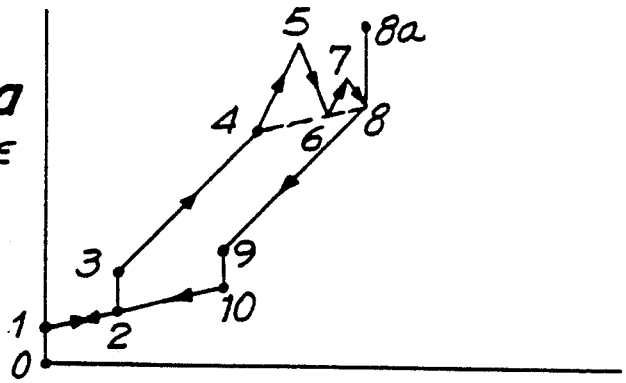
FIGS. 22a, 22b, 22c and 22d are charts representing the former force, former spring force, anvil spring force, and anvil travel requirements of this invention.
Figure 22B:
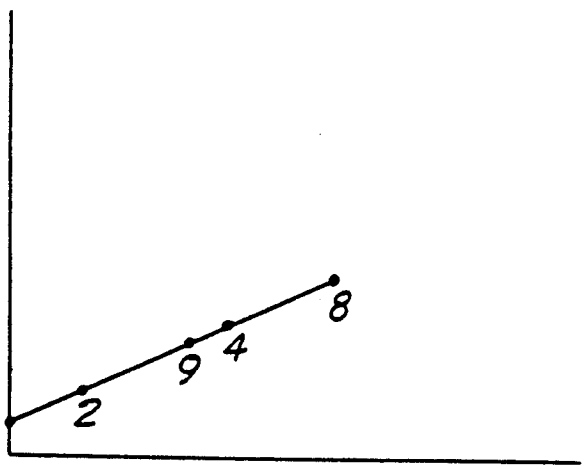
Figure 22C:
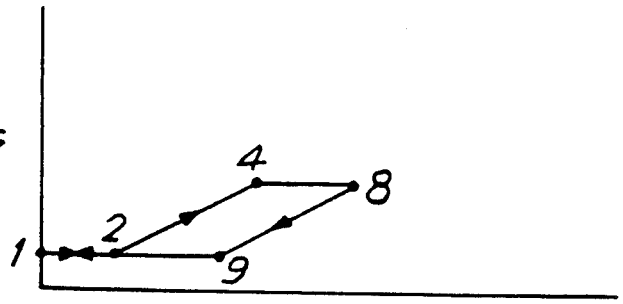
Figure 22D:
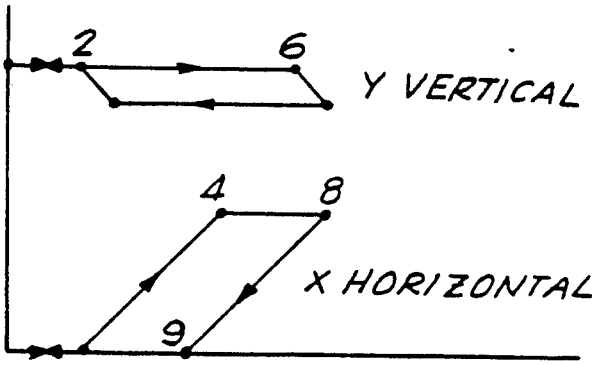

The force required to move the former varies throughout the cycle. The former force, former spring force, anvil spring force, and anvil travel requirements are shown in FIG. 22(a)–(d), respectively. Each phase of the former force requirements of FIG. 22(a) are described in detail below.

| PHASE | DESCRIPTION |
|---|---|
| 0-1 | Force required to overcome the former return spring pre-load. |
| 1-2 | Former advance to turn staple. |
| 2-3 | Force increase to overcome anvil return spring pre-load. |
| 3-4 | Former advance to advance staple and lower anvil to upper anvil location. Both former and anvil return spring forces increase. |
| 4-5-6 | Staple formed. |
| 6-7-8 | Lower anvil stripped. |
| 8a | Setting of staple. |
| 8-9 | Former and lower anvil return together. |
| 9-10 | Lower anvil return spring pre-load unloaded against home stop. |
| 10-2-1 | Former returns to home position. |
| 1-0 | Former return spring pre-load unloaded against former home stop. |

Figure 23A:
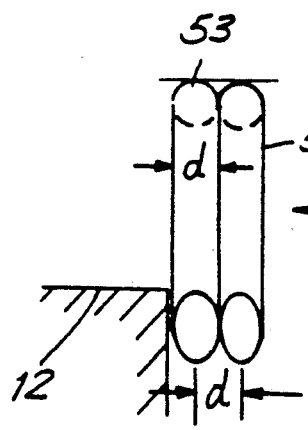
FIGS. 23a and b are schematic representations illustrating the staple stack support system of this invention.
Figure 23B:
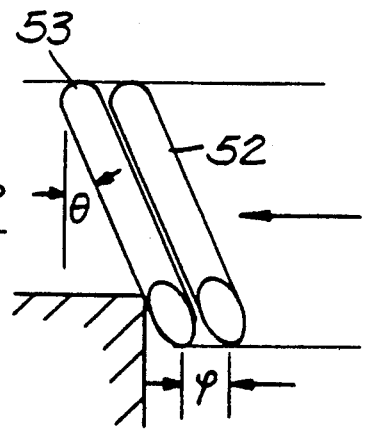

The present invention also provides a unique support for the staple stack. In the present invention, the staple stack remains stationery while the lower anvil and former advance even though the pusher spring 94 is applying pressure to the rear of the stack tending to advance the stack forward. Referring now to FIG. 23a, in this invention, the leading staple abuts an edge of case 12. This edge holds back the entire stack of staples even though the pusher spring force is urging the staples forwardly. FIG. 23b illustrates why the stack does not shingle causing the stack to collapse. In order for the condition of FIG. 23b to occur, the spacing between staples would need to increase to a value given by: $p = d/\cos\theta$ where d equals the staple diameter. If the stack shingles, as shown in FIG. 23b, the space occupied by the stack would increase and, consequently, the pusher spring 94 would compress. The pusher spring 94, therefore, prevents the stack from shingling and it remains stationary as is shown in FIG. 23a. As shown in FIG. 12, the aforementioned rail step 71 also abuttingly retains the cross-arm of the stack of staples.

Another major improvement is the staple advance mechanism within the stapler assembly. The lower anvil 98 is advanced by the former 114 and returned by a spring. The methods of providing this return spring action are described below.

Figure 25A:
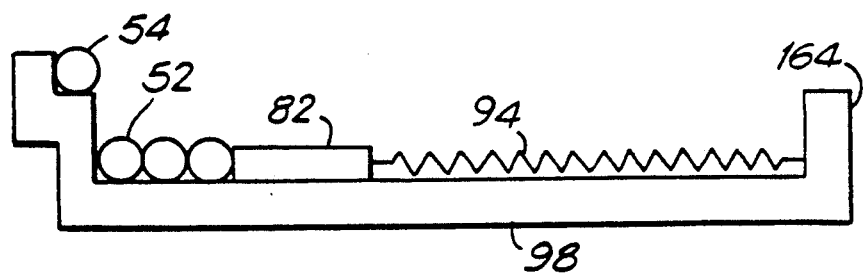
FIG. 25a, b, c, and d are schematic representations illustrating various methods of providing for the lower anvil return spring force for this invention.

In the first method, as shown in FIG. 25a, the staple stack pusher spring 94 bears against a bent up tab 164 of lower anvil 98 at the opposite end of lower anvil 98 from the staple forming surface 108. This spring acting on the bent up tab of anvil 98 and the pusher provides both the stack advance pressure as well as the anvil return spring force.

Figure 25B:
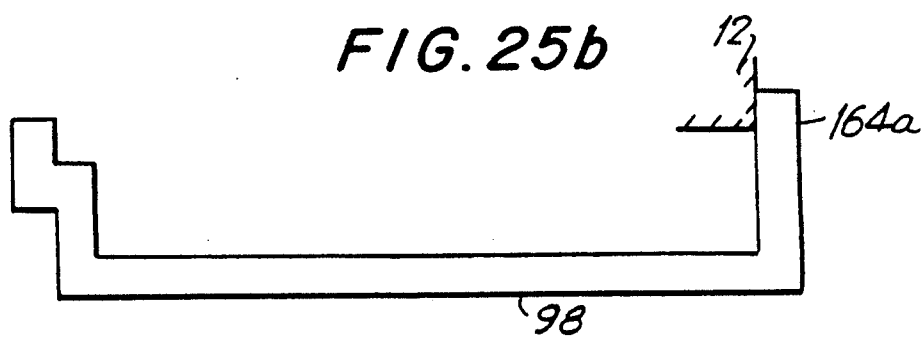
Figure 25C:
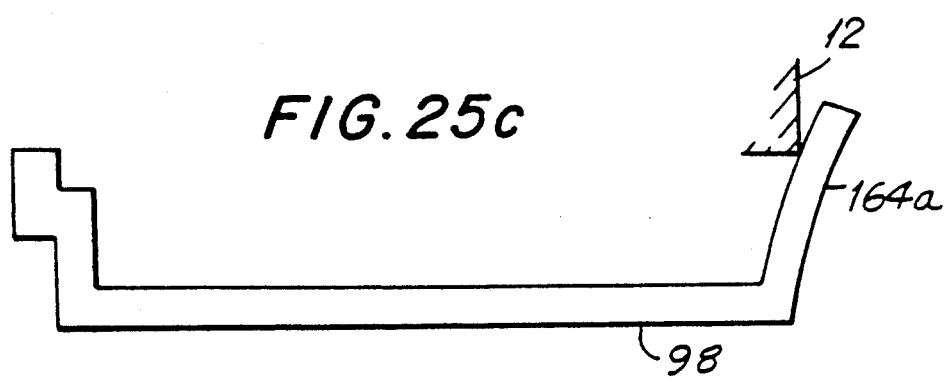

In the second method (as shown in FIGS. 25b and c), the lower anvil 98 is anchored to case 12 by means of a bent up tab 164a, similar to the previous bent up tab 164 which flexes, sufficient to accommodate the lower anvil 98 motion.

Figure 25D:
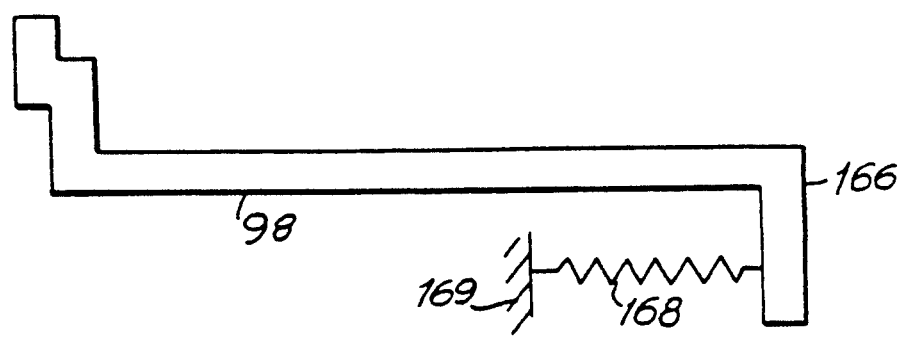

In the third method (see FIG. 25d), the lower anvil 98 is provided with a downwardly extending tab 166 at an end opposite to staple forming surface 108. A dedicated or anvil return spring 168 is provided in biasing engagement with downwardly extending tab 166 to provide the return action of the lower anvil 98.

In accordance with one of the general objects of the present invention, it is desirable to provide a latch to interrupt the trigger just prior to staple formation. This locks the staple mechanism against the action of the return springs and allows the user to comfortably position the staple points, which are fully visible, for insertion. As is shown in FIGS. 26-27, the preview latch 170 includes a flex arm 172 molded as part of one side of the split case housing 12. This arm is flat and thin in the lateral direction allowing easy flexing. The tip 174 of flex arm 172 has a hooked section 176 for hooking or latching onto a latch recess 178 in a raised cam feature 180 molded into trigger 16.

In the process of squeezing trigger 16, the flex arm 172, as best shown in FIG. 27, contacts a first camming surface 180 of cam 178. This first camming surface 180 guides and flexes the flexed flex arm 172 laterally into the latch edge 178 just prior to staple formation. At this point, the trigger may be released and the flex arm hooked on the trigger cam will hold the case and trigger at a constant relative position against the action of the trigger return spring. As such, the user may comfortably position the staple points, which are fully visible, for insertion.

After the user is satisfied that the staple points are in the proper position, further actuation of trigger 16 causes the flex arm 174 to become disengaged from latch edge 179 and be guided by second camming surface 182 of cam 178 to return to its home position.

U.S. Pat. No. 4,691,853 describes a stapler with a fixed pivot trigger having a relatively constant mechanical advantage through its stroke. The force required, however, in the current improvement varies from a low value early in the forward stroke to a high value during staple forming and setting at the end of the forward stroke. As such, applicant has designed a unique "variable ratio trigger" in order to accommodate the varying force requirements of this stapler.

In a fixed mechanical advantage device, such as a stapler with a fixed pivot trigger, a long stroke is achieved at low mechanical advantage. High mechanical advantage can be achieved only by reducing the stroke. It is, therefore, desirable to have a variable mechanical advantage. A trigger incorporating a variable mechanical advantage during actuation is referred to as a "variable trigger ratio." With such a feature, the variable or varying former force requirements are transformed into more constant trigger force requirement.

As is shown in FIG. 28, in order to achieve this result, the trigger 16 is molded with two cam tracks 184a and 184b which engage two pin projections 186a and 186b, respectively, molded into the two halves 13a and 13b of case 12. The cam tracks are shaped so as to cause the ball 144 which engages load button 146 which drives the former to move in a straight line as trigger 16 rotates. The relationship between the rotation of the trigger and the advance of the former contact points can be varied by design to produce the desired varying mechanical advantage.

In use, the trigger motion is determined by the shape of the cam tracks. By proper design of the shape of the two cam tracks, any desired program of rotation of trigger and linear trigger advance may be achieved. The staple trigger is actuated by the user's hand. It in turn drives the former 114 forward to accomplish the forward stroke of the cycle. The former requires a certain minimum travel to complete the functions of rotate, advance, form, strip, and set. The trigger size and travel is constrained by the requirement that a normal size hand be comfortably able to grasp it. Furthermore, the force required of the hand must not exceed a certain maximum to avoid discomfort and fatigue.

To make best use of the trigger travel available, it is useful to design the ratio between the trigger travel and former travel to match the need for force leverage or mechanical advantage during the cycle. In this case, it is lower during the early part of the cycle and greater during the later part when the staple is being formed and stripped. The trigger advance, hence, should move the former rapidly at first with a low mechanical advantage when the former force requirement is low and slowly as the staple is being formed when the force requirement is high. A simple trigger pivoting around a fixed pivot point cannot tailor the mechanical advantage to that desire to achieve compromise between the trigger travel available and former force required. A cam drive in accordance with this invention can provide the variable ratio action desired.

Furthermore, the rotation versus advance program shown in FIG. 29, is desired where:
  (a) full trigger rotation is denoted by $\theta_m$;
  (b) full trigger linear advance is denoted by $X_m$; and
  (c) the relationship between rotation and advance is non-linear as shown where the advance versus rotation is high at first and lower later in the stroke.

The inverse of the slope of the curve of FIG. 29 is the mechanical advantage.

The use of the cam tracks in the preferred embodiment of this invention provides for movement of the former rapidly in a straight line motion at first with a low mechanical advantage when the former force requirement is low and slowly as the staple is being formed when the force requirement is high.

Figure 30:
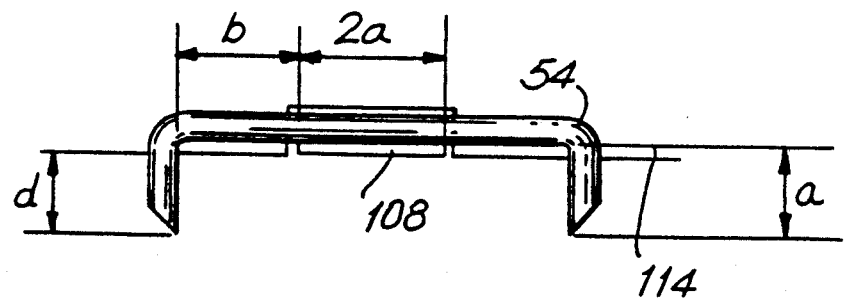
FIGS. 30, 31 and 32 are schematic illustrations of conventional methods of forming a staple for insertion into tissue.
Figure 31:
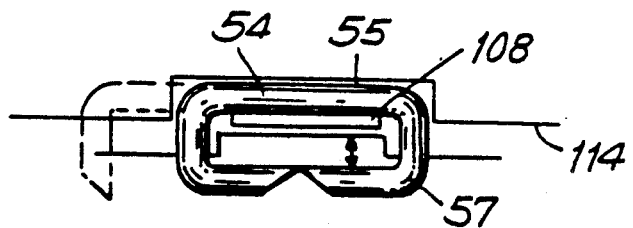
Figure 32:
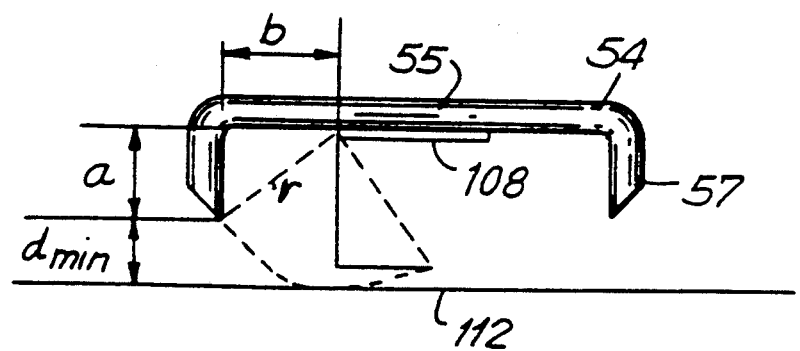
Figure 33:
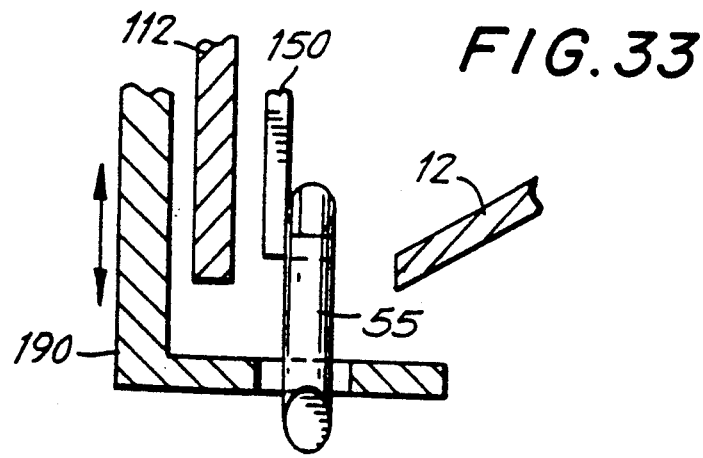
FIG. 33 is a side elevational view of one embodiment of a tissue shield for varying the amount of tissue approximation.
Figure 34:
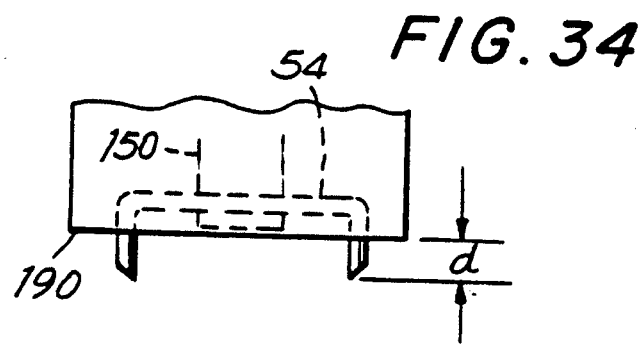
FIGS. 34 and 35 are top elevational views illustrating the use of the tissue shield of FIG. 40 to vary tissue approximation.
Figure 35:
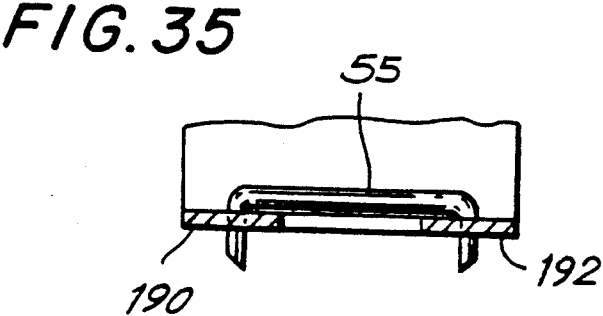
Figure 36:
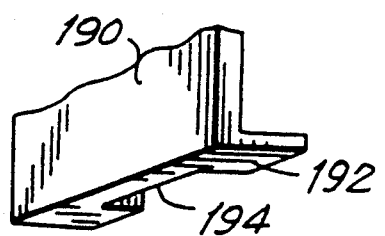
FIG. 36 is a front perspective view of the tissue shield opening for the tissue shield of FIG. 35.

In the field of surgical staplers, the conventional method of forming the staple for insertion into tissue is shown in FIGS. 30-32. In the conventional formation process, the staple bends at point A. The staple point B follows a circular path of radius $\sqrt{a^2+b^2}$ shown in FIG. 31. Staple formation occurs with the staple located relative to the housing in FIG. 31. In this configuration, the staple points protrude below the lower portion of the housing by an amount "d". That dimension together with the staple geometry and any forceps induced tissue effects determines the level of tissue within the perimeter of the formed staple. After the staple has been formed, the level of tissue within the closed staple is denoted by H in FIG. 31. In conventional staplers, these conditions are fixed by design. In the present invention, however, these conditions are controlled or selectable by the surgeon. The advantage of being able to select the amount of tissue contained within the formed staple is that whereas in conventional staplers the depth of the staple insertion is variable according to the force with which the staple is pressed against the tissue, in this invention, the surgeon may adjust the stapler to accommodate his own preferred technique. As such, adjusting the instrument to the user is preferable to having to adjust the user's own surgical techniques.

There is a variety of reasons for the surgeon desiring to control the inserted staple condition. These include accommodating varying degrees of tendency to press the stapler against the skin, the variability of skin thickness in different areas (e.g. neck versus stomach) and the desire to avoid crosshatching the skin across the wound gap by the staple cross-arm.

In conventional staplers, the dimension "d" shown in FIG. 32 is fixed by design and determined by the physical relationship of the anvil to the housing. This design dimension is chosen experimentally to achieve a balance between too little approximation for a small or negative value of "d" and too great an approximation of tissue for to large a value of "d". There is a value of "d" for which no tissue approximation occurs. This relationship is shown in FIG. 32. The value of "d" denoted "$d_{min}$" for which no tissue approximation occurs is given by the equation: $d_{min} = \sqrt{a^2+b^2} - a$. As the surface A shown in FIG. 32 is moved upwardly, the staple points are able to gather in increasing amounts of tissue. The value of "d" in excess of "$d_{min}$" determines the distance below the surface A which the staple points attain in swinging from the fully open pre-formed condition of FIG. 32 to the fully closed or formed condition of FIG. 31.

This invention is advantageous to the conventional stapler in that the selection of "d" is left to the surgeon who may increase or decrease the distance "d" to suit his technique and existing surgical conditions during the wound closure procedure to achieve a more effective end result.

In one preferred embodiment for a tissue approximation technique as shown in FIGS. 33-36, in order to control the distance "d", the surgical stapler includes a slidable tissue shield 190 secured to top face 34 of case 12. Tissue shield 190 which may be slidably positioned relative to the staple points so as to adjust the dimension "d" thereby adjusting the amount of tissue approximation. Tissue shield 190 includes a tissue shield opening 194 (See FIG. 36) which provides for sufficient clearance to allow staple ejection.

The tissue shield may be adjusted relative to the staple at the anvil position of staple formation by various means including many conventional kinematic mechanisms such as gears, screws and cams. Examples of each are shown in FIGS. 37a-d. Each mechanism provides an adjustable link 196a, b, c and d, respectively, which the surgeon uses to position the tissue shield. The motion of the adjustment link provides for relatively small position adjustments of the tissue shield which are required. For example, a typical staple is shown in FIGS. 38a-c, before and after forming. For this staple, the zero approximation shield position is 0.04 inches below the points. The maximum approximation shield position is also shown in FIG. 38b at the level of the staple cross-arm. The full range of adjustment is thus 0.14 inches. This small adjustment cannot be controlled comfortably without a mechanism to amplify it to an adjustment range compatible with surgeon's sense of adjustment or ability to control motion. In the case of a linear adjustment link, such as shown in FIG. 37d an adjustment link motion of approximately 0.5 inches is required to control the tissue shield movement of 0.14 inches. For rotary adjustment links, such as shown in FIGS. 37c, the rotary input range should be approximately 180° for the required shield movement of 0.14 inches.

As is shown in FIG. 37a, in the case of a gearing mechanism controlling the tissue shield, the adjustment link movement is linear. This movement is geared down to advance the tissue shield at a reduced rate. If the controlling mechanism is in the form of a screw, the nut 198, as shown in FIG. 37b, is rotated while being prevented from advancing. The tissue shield cannot rotate. Consequently, it advances as nut 198 is rotated.

If the controlling mechanism is a rotary cam, such as 200 in FIG. 37c, the tissue shield is advanced by a close fitting rotary cam within a cam slot 202. The cam is rotated about a center eccentric to its own. This mechanism is sometimes referred to as a "scotch yoke". Finally, if the controlling mechanism is a linear cam such as 204 in FIG. 37d, the fixed housing 206 contains an inclined slot 208. The tissue shield contains a second slot 210 at a small angle to slot 208. The adjustment link 196d, a slide which engages both slots, moves from position 1 to 4. As it moves, the tissue shield is appropriately advanced.

Figure 39A:
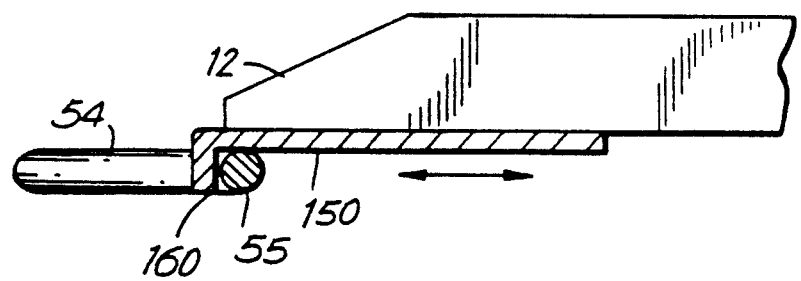
FIGS. 39a and b are side elevational view illustrating another preferred embodiment of this invention to provide tissue approximation.
Figure 39B:
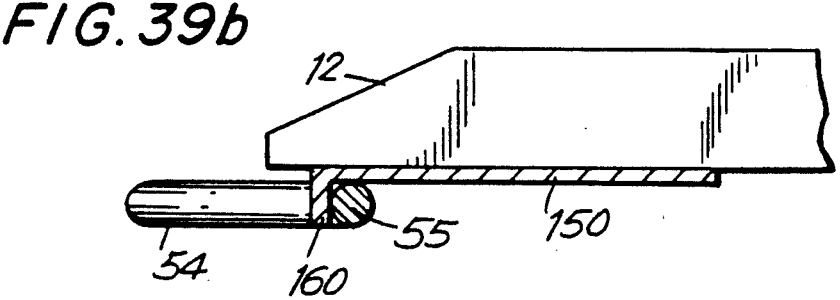
Figure 40A:
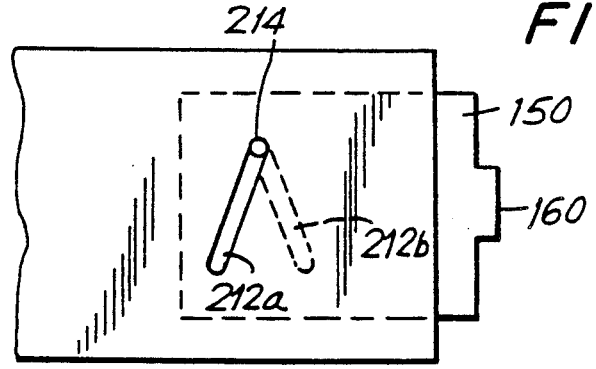
FIGS. 40a and b are top elevational views illustrating the tissue approximation method of FIGS. 39a and b wherein a slide button cams the upper anvil in and out.
Figure 40B:
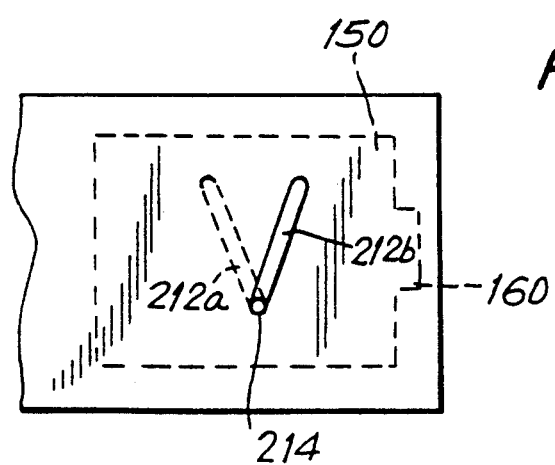

In another preferred embodiment for a variable tissue approximation technique for this invention, since the upper anvil location determines the place where the staple is formed, by making the upper anvil location variable, as is shown in FIGS. 39a and b, case 12 acts to shield the tissue varying the degree of tissue approximation. In this method of adjusting the upper anvil location, an inclined cam technique is preferable wherein a slot 212a on case 12 and another slot 212b on upper anvil 150 are coupled via a slide button 214 (See FIGS. 40a and b). The shallow angle insures that the upper anvil does not move during staple formation through the mechanism of frictional lock-up. As the button is slid from side to side, upper anvil 150 is cammed in and out to thereby vary the distance between the upper anvil and the staple points.

As shown herein, all functions of the device (turning, transporting, forming, stripping and loading) are accomplished as part of the continuous mechanical action. This invention allows the manufacturing of a surgical stapler wherein the stack of staples 52 is configured in a typical orientation as those of a conventional paper stapler. The present invention also includes a means for transporting turning, stripping and forming the leading staple so that the staple may be directed perpendicular to the tissue to be closed and that stapler may be used by the surgeon at approximately 45° to the surface of the skin.

In addition, the present invention provides a surgical stapler in which the staple is advanced so that rotation occurs within the housing, the staple is set at the end of the forward stroke and the staple is released on the return stroke of the former. In addition, this surgical stapler provides for a varying mechanical advantage to accommodate the staple advance at a reasonable hand force level and also provides for varying the amount of tissue which is drawn up or approximated within the perimeter of the form staple.

To produce the proper movement pattern of parts for turning, transporting, forming, stripping, and loading of the staples, many different mechanisms may be devised. However, the preferred embodiments disclosed herein are not only remarkably simple to manufacture and use, they are designed to be extremely inexpensive to produce, while still meeting all the objectives described in the earlier paragraphs.

While the preferred embodiments of the present invention have been described, it should be understood that various changes, adaptations and modifications may be made therein without departing from the spirit of the invention and the scope of the appended claims.

What is claimed is:

1. A stapling device for use in ejecting a single staple to close an incision or wound comprising:
   a case including a staple discharge area;
   a cartridge assembly adapted to receive a plurality of staples in a generally stacked planar arrangement disposed within said case at a first plane;
   a pusher assembly engageable with said stack of staples and movable between a first rearward position and a second forward position to advance said stack of staples;
   control means for turning a single staple around an axis generally normal to said stack of staples to form a turned staple, wherein said turned staple is at a second plane other than the first plane of the stack of staples;
   means for moving said turned staple at a predetermined distance within the device;
   forming means for forming the staple into a closed gripping configuration;
   stripping means for disengaging the staple to be ejected from the device; and
   loading means for loading a single staple within said stack of staples into a position to be turned.

2. The stapling device according to claim 1 wherein the stripping means comprises:
   a former including a cam extending downwardly therefrom and means to restrain said formed staple;
   a first anvil having a base, a cam follower surface projecting upwardly from said base, a staple stack retainer surface extending upwardly from an end of said base, and a staple transport surface extending outwardly from an end of said staple stack retainer surface upon which said plurality of staples are transported; and a staple forming surface extending upwardly from said staple transport surface, and
   said first anvil being displaceable between a rest position and a flexed position wherein said staple is disengaged from said staple forming surface as said first anvil is pivoted downwardly and is restrained from downward movement with said anvil by said means to restrain said formed staple.

3. The stapling device according to claim 2 wherein said means to restrain said formed staple includes a pair of arms extending outwardly from said former, said arms having leg retainer edges which restrain longitudinal movement of the staple when said first anvil is displaced to its flexed position.

4. The stapling device according to claim 2 wherein said cam engages said cam follower when said former is advanced forwardly to cantilever downwardly said first anvil to disengage the staple from said staple forming surface.

5. The stapling device according to claim 1 wherein said loading means comprises:
   a means for advancing said stack of staples;
   a first anvil having a base; a cam follower surface projecting upwardly from said base; a staple stack retainer surface extending upwardly from an end of said base; a staple transport surface extending generally outwardly from an end of said staple stack retainer surface; and a staple forming surface extending generally upwardly from an end of said staple transport surface;
   a former including means for engaging said cam follower surface;
   said first anvil being displaceable between a flexed position wherein said means for engaging said cam follower engages said cam follower so that said staple transport surface receives the leading staple of the stack of staples and a return position wherein said staple is moved upwardly into a position to be turned.

6. A stapling device for use in ejecting a single staple to close an incision or wound comprising:
   a case having a bottom and a top side and a staple discharge area,
   a cartridge assembly adapted to receive a plurality of staples in the form of a stack in a generally planar arrangement disposed within said case at a first plane,
   a pusher assembly engageable with said stack of staples and movable between a first rearward position and a second forward position to advance said stack of staples,
   control means for turning a single staple of the stack of staples from a first position to a second position at a significant angle to said first position to form a turned surface, wherein said turned staple is positioned at a second plane other than the first plane of the stack of staples,
   transporting means for moving a single staple to be ejected within the device such that the staple can be discharged from the device at a significant angle less than 90° from the incision or wound,
   forming means for forming the staple into a closed gripping configuration, and
   stripping means for disengaging the staple to be ejected from said device and to eject the fully formed staple.

7. The stapling device according to claim 6 wherein the stripping means comprises:
   a former including a cam extending downwardly therefrom and a means to restrain said formed staple;
   a first anvil having a base, a cam follower surface projecting upwardly from said base, a staple stack retainer surface extending upwardly from an end of said base, and a staple transport surface extending generally outwardly from an end of said staple stack retainer surface upon which said plurality of staples are transported; and
   said first anvil being displaceable between a rest position and a flexed position wherein said staple is disengaged from said staple forming surface as said first anvil is pivoted downwardly and restrained from downward movement with said first anvil by said means to restrain said formed staple.

8. The stapling device according to claim 7 wherein said means to restrain said formed staple includes a pair of arms extending outwardly from said former, said arms having leg retainer edges which restrain movement of the staple downwardly when said first anvil is displaced to its flexed position.

9. The stapling device according to claim 7 wherein said cam engages said cam follower surface when said former is advanced forwardly to cantilever downwardly said first anvil to disengage the staple from said staple forming surface.

10. The stapling device according to claim 6 and further includes:
   a loading means for loading single staple within a stack of staples into a position to be turned.

11. The stapling device according to claim 10 wherein said loading means comprises:
   a means for advancing said stack of staples;
   a first anvil having a base; a cam follower surface projecting upwardly from said base; a staple stack retainer surface extending upwardly from an end of said base; a staple transport surface extending generally outwardly from an end of said staple stack retainer surface; and a staple forming surface extending generally upwardly from an end of said staple transport surface;
   a former including a means for engaging said cam follower surface;
   said first anvil being displaceable between a flexed position wherein said means for engaging said cam follower engages said cam follower so that said staple transport surface receives the leading staple of the stack of staples and a return position wherein said staple is moved upwardly into a position to be turned.

12. The stapling device according to claim 11 wherein said means for advancing said stack of staples is a pusher spring means for displacing said pusher between its rearward and forward positions.

13. The stapling device according to claim 12 wherein:
   said first anvil includes an upwardly extending tab at one end thereof opposite to said staple forming surface.

14. The stapling device according to claim 13 wherein said pusher spring means is biased between said pusher and said upwardly extending tab thereby providing both the stack advance pressure as well as an anvil return spring force.

15. The stapling device according to claim 13 wherein said upwardly extending tab is in abuttable engagement with and a surface of said case to thereby provide an anvil return spring force.

16. The stapling device according to claim 12 wherein said first anvil includes a downwardly extending tab at one end thereof opposite to said staple forming surface.

17. The stapling device according to claim 16 wherein said downwardly extending tab is in biasing engagement with a first anvil return spring to thereby provide an anvil return spring force.

* * * * *